US011512003B2

(12) United States Patent
Lux et al.

(10) Patent No.: US 11,512,003 B2
(45) Date of Patent: Nov. 29, 2022

(54) METHOD FOR SYNTHESIZING SILICA NANOPARTICLES

(71) Applicants: NH THERAGUIX, Villeurbanne (FR); Universite Claude Bernard Lyon 1, Villeurbanne (FR); Centre National de La Recherche Scientifique—CNRS, Paris (FR)

(72) Inventors: François Lux, Lyons (FR); Olivier Tillement, Fontaines Saint-Martin (FR); Fabien Rossetti, Villeurbanne (FR); Vivek Thakare, Nasik (IN); Vu Long Tran, Ho Chi Minh (VN)

(73) Assignees: NH THERAGUIX, Villeurbanne (FR); Universite Claude Bernard Lyon 1, Villeurbanne (FR); Centre National de La Recherche Gantifote—CNRS—, Paris (FR)

( * ) Notice: Subject to any disclaimer, the term of this patent is extended or adjusted under 35 U.S.C. 154(b) by 63 days.

(21) Appl. No.: 16/620,413

(22) PCT Filed: Jun. 8, 2018

(86) PCT No.: PCT/EP2018/065242
§ 371 (c)(1),
(2) Date: Dec. 6, 2019

(87) PCT Pub. No.: WO2018/224684
PCT Pub. Date: Dec. 13, 2018

(65) Prior Publication Data
US 2021/0078867 A1 Mar. 18, 2021

(30) Foreign Application Priority Data

Jun. 9, 2017 (EP) ..................................... 17305701
Feb. 16, 2018 (EP) ..................................... 18305165

(51) Int. Cl.
*C01B 33/18* (2006.01)
*A61K 49/08* (2006.01)
(Continued)

(52) U.S. Cl.
CPC ............ *C01B 33/183* (2013.01); *A61K 49/08* (2013.01); *A61K 49/106* (2013.01);
(Continued)

(58) Field of Classification Search
None
See application file for complete search history.

(56) References Cited

U.S. PATENT DOCUMENTS

2009/0087381 A1  4/2009  Ding et al.
2010/0266491 A1* 10/2010  Farokhzad ......... A61K 47/6937
424/1.29
(Continued)

FOREIGN PATENT DOCUMENTS

WO   WO 2007/124131 A2   11/2007
WO   WO 2010/030119       3/2010
(Continued)

OTHER PUBLICATIONS

Bagwe et al., "Surface Modification of Silica Nanoparticles to Reduce Aggregation and Nonspecific Binding", *Langmuir*, vol. 22 (9), p. 4357-4362, (2006).
(Continued)

*Primary Examiner* — Colin W. Slifka
*Assistant Examiner* — Michael Forrest
(74) *Attorney, Agent, or Firm* — Hoxie & Associates LLC

(57) ABSTRACT

The invention relates to a method for synthesizing ultrasmall silica nanoparticles, useful in particular for diagnostics and/or therapy. More specifically, a method for synthesizing silica nanoparticles, said method comprising the mixing of at least one silane which is negatively charged at physi-
(Continued)

ological pH with at least one silane which is neutral at physiological pH, and/or at least one silane which is positively charged at physiological pH, wherein: —the molar ratio A of neutral silane(s) to negatively charged silane(s) is defined as follows: $0 \leq A \leq 6$, —the molar ratio B of positively charged silane(s) to negatively charged silane(s) is defined as follows: $0 \leq B \leq 5$, —the molar ratio C of neutral and positively charged silanes to negatively charged silane(s) is defined as follows: $0 < C \leq 8$. The invention also relates to the obtained ultrasmall silica nanoparticles.

19 Claims, 15 Drawing Sheets

(51) Int. Cl.
    *A61N 5/10*     (2006.01)
    *A61K 49/18*     (2006.01)
    *A61K 49/10*     (2006.01)
    *B82Y 30/00*     (2011.01)
    *B82Y 40/00*     (2011.01)
(52) U.S. Cl.
    CPC ...... *A61K 49/1833* (2013.01); *A61K 49/1881* (2013.01); *A61N 5/1039* (2013.01); *A61K 49/183* (2013.01); *B82Y 30/00* (2013.01); *B82Y 40/00* (2013.01); *C01P 2004/64* (2013.01)

(56) References Cited

U.S. PATENT DOCUMENTS

2010/0278734 A1* 11/2010 Bonitatibus, Jr. .. A61K 49/1848
    424/9.1
2015/0050217 A1* 2/2015 Cremillieux ............ A61P 35/00
    424/9.2

FOREIGN PATENT DOCUMENTS

WO     WO 2011/135101 A2     11/2011
WO     WO 2012/100174     7/2012

OTHER PUBLICATIONS

Bronstein et al., "Functional Polymer Colloids with Ordered Interior", *Langmuir*, vol. 20 (4), p. 1100-1110 (2004).

El-Nahhal et al., Ä review on polysiloxane-immobilized ligand systems: Synthesis, characterization and applications, *Journal of Organometallic Chemistry*, vol. 692, p. 2861-2886 (2007).

* cited by examiner

Emission spectrum of DOTAGA(Eu$^{3+}$) at 40 μM

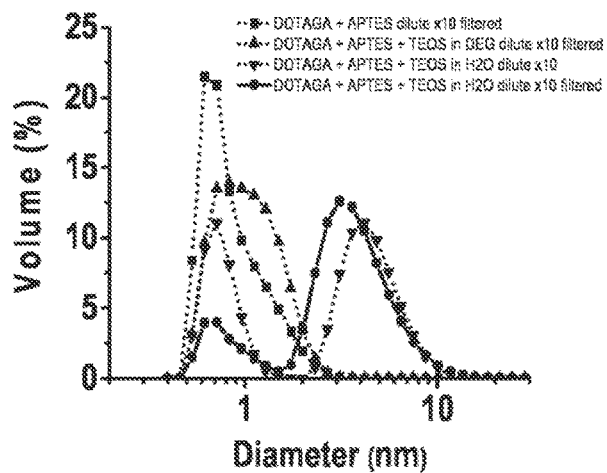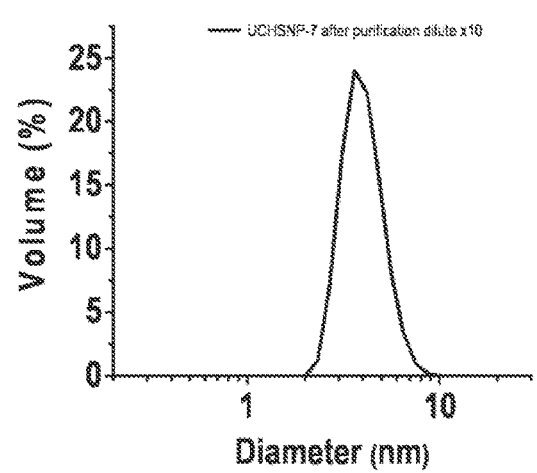
FIG. 21A                       FIG. 21B
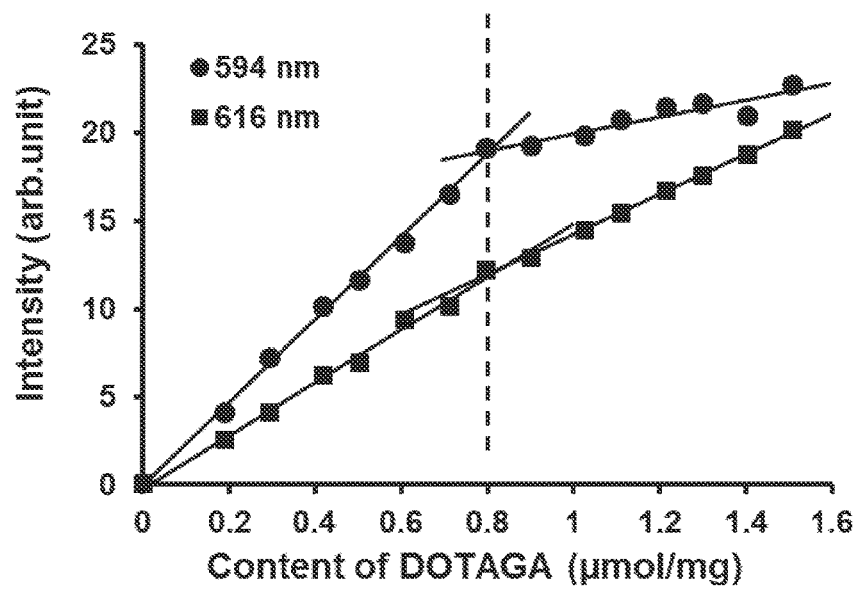
Figure 22

METHOD FOR SYNTHESIZING SILICA NANOPARTICLES

CROSS REFERENCE TO RELATED APPLICATIONS

This application is a United States Application under 35 U.S.C. 371 claiming benefit of PCT Application No. PCT/EP2018/065242, filed on Jun. 8, 2018, which claims the benefit of European Patent Application No. 17305701.9, filed on Jun. 9, 2017 and European Patent Application No. 18305165.5, filed on Feb. 16, 2018, the contents of each of which are incorporated herein by reference.

Technical Domain

This invention relates to a method for synthesizing ultrasmall silica nanoparticles, useful in particular for diagnostics and/or therapy. The invention also relates to the obtained ultrasmall silica nanoparticles.

Technological Background

Cancer is a major cause of death in many countries in the world. Today, there are three main methods to treat cancer which are surgery, chemotherapy and radiotherapy. The latter implies the use of ionizing radiations to destroy the cancerous cells in the tumors. However, an important side effect of radiotherapy is that the irradiation can also damage the normal tissues surrounding the tumors. Although much technological advancement has been made in the design of beam shapes and in the treatment planning, this side effect still limits the therapeutic windows of radiotherapy. Two main strategies have been introduced to overcome this side effect: using different particles such as protons, neutrons or heavy ions instead of conventional photons, and/or using a radiosensitizer to locally enhance the delivered dose within the tumors. The latter opens the door for researches on new materials which can act as effective sensitizers.

Another prerequisite in the battle against cancer is to precisely localize the tumors. Currently, there are several imaging techniques that can be used for this purpose including MRI, X-ray CT, scintigraphy which is comprised of single photon emission computed tomography (SPECT) and positron emission tomography (PET), optical imaging and ultrasound imaging. These techniques also require new materials as probes or contrast enhancing agents to improve the quality of images. Besides, each technique has its own advantages and drawbacks; therefore, the combination of complementary techniques, which is so called multimodal imaging, to achieve both high resolution and sensitivity is an active research field.

In recent years, the emergence of nanotechnology offered tremendous opportunities for developing new solutions for modern medicine, especially cancer treatment. This created a fast emerging field called nanomedicine in which one of the most promising research directions is the development of nanomaterials as new types of therapeutic agent or new types of probes or contrast agents for imaging. This is due to numerous novel advantages that nanoparticles can offer such as:
  the ability to protect, deliver and release a large amount of active molecules to some specific sites based on the chemical design of the nanoparticles;
  the possibility of combining different elements, like active molecules, functionalized group or imaging probes, in only one nanoparticle;
  the ability to target specifically the cancerous tumors thanks to the EPR effect "Enhanced Permeability and Retention", which is the tendency of nanoparticles to accumulate in the tumors rather than in normal tissues;
  the optical, thermal, magnetic and electronic properties of nanomaterials induced by their nanometric sizes.

Among the different types of nanoparticles, the ones containing metals attract a lot of interests. This type of nanoparticles allows taking advantage of several valuable properties of metals such as radiosensitizing ability of high Z metals e.g. Au (Z=79), Pt (Z=78), Hf (Z=72), Gd (Z=64) or paramagnetic property of gadolinium (Gd) for MRI imaging, or nuclear particle emission e.g. $^{64}$Cu, $^{68}$Ga, $^{99}$Tc, $^{89}$Zr, $^{111}$In for scintigraphy imaging, $^{90}$Y or $^{177}$Lu for curie therapy. Several examples have been described in literature. In particular, silica nanoparticles have been intensively studied as a nanocarrier for different metals. They are safe and easy to be synthesized and functionalized. Additionally, in many cases, they do not interfere with the interaction between metals and external stimuli, e.g. radiation particles, optical beams etc.

Patent application WO2007124131 describes silica nanoparticles that are functionalized with chelators, i.e. DTTA, DTPA, and used in clinics for chelating $Gd^{3+}$ as a contrast agent. The hydrodynamic diameters (DH) of these nanoparticles are in the order of 40 nm. However, recently, many studies have shown that an ultrasmall size with DH inferior to 10 nm is recommended for nanoparticles to be quickly and completely eliminated from the body through urine. This will prevent long term toxicity of metal, like $Gd^{3+}$ which is notorious for nephrogenic systemic fibrosis as a severe side effect. Furthermore, minimizing the size of particles creates a larger surface and therefore a much higher loading rate of Gd chelates.

Nevertheless, it is still difficult to synthesize nanoparticles of this size, i.e. with an ultrasmall DH, for example inferior to 15 nm, preferably inferior to 10 nm.

Patent application WO2011135101 A2 describes a Gd-based silica nanoparticle, also known as AGuIX®, which shows promising results for being used as a theranostic agent. This nanoparticle comprises a polysiloxane network functionalized with chelators like DOTAGA and has a DH which is smaller than 5 nm. Most of the chelators (usually more than 50%) on the particle form a complex with $Gd^{3+}$. This nanoparticle is a very efficient contrast agent for tumor detection using MRI. Also, all of its components i.e. polyorganosiloxane, $Gd^{3+}$ complex of DOTAGA are known to be safe for humans. AGuIX® is quickly eliminated from the human body through renal clearance which helps to prevent the deposit of $Gd^{3+}$ in organs, and therefore, a severe long term complication known as nephrogenic systemic fibrosis.

Nevertheless, the synthesis of this nanoparticle is not straightforward as it is done via a multistep synthesis as presented in FIG. 1. First, a small, 1 to 3 nm, gadolinium oxide core is synthesized in diethylene glycol (DEG). Then, this core is coated with a layer of polyorganosiloxane by hydrolysis and condensation reaction of alkoxysilane. Next, this layer is functionalized with DOTAGA anhydride. After that, the nanoparticle is transferred to water in order to dissolve the core and release $Gd^{3+}$ ions, which are chelated by DOTAGA. After fragmentation of the polysiloxane layer, the nanoparticles are obtained. This top-down method has been well studied, however, it is time-consuming, solvent-consuming and raw materials-consuming. Besides, it implies a low yield and difficulty to change or add different metals post-synthetically.

Therefore, it would be desirable to develop an easier method to synthesize this nanoparticle which could overcome the limits of the current synthesis. In particular, it would also be desirable to develop a one-pot synthesis method enabling the production of ultrasmall and stable silica nanoparticles. Moreover, it would also be desirable that this new method enables the synthesis of nanoparticles with a high loading rate of empty chelators which can then be chelated by different metals depending on the application.

BRIEF DESCRIPTION

A first aspect of the present disclosure relates to a method for synthesizing silica nanoparticles, said method comprising the mixing of at least one silane which is negatively charged at physiological pH with
- at least one silane which is neutral at physiological pH, and/or
- at least one silane which is positively charged at physiological pH,
wherein:
- the molar ratio A of neutral silane(s) to negatively charged silane(s) is defined as follows: $0 \leq A \leq 6$, preferably $0.5 \leq A \leq 2$;
- the molar ratio B of positively charged silane(s) to negatively charged silane(s) is defined as follows: $0 \leq B \leq 5$, preferably $0.25 \leq B \leq 3$;
- the molar ratio C of neutral and positively charged silanes to negatively charged silane(s) is defined as follows: $0 < C \leq 8$, preferably $1 \leq C \leq 4$.

Another aspect of the disclosure relates to a silica nanoparticle having a hydrodynamic mean diameter of between 0.5 and 15 nm, for example between 0.5 and nm, comprising a polyorganosiloxane matrix which is grafted with chelating agents, said chelating agents being free of metallic ions and present at a content of at least 0.1 µmol/mg of nanoparticle, preferably between 0.5 and 2 µmol/mg. For example, in one specific embodiment, the chelating agent is DOTAGA and the content of the chelating agent is comprised between 0.5 and 2 µmol/mg.

DETAILED DESCRIPTION

Method for Synthesizing Silica Nanoparticles

In a first aspect, the present disclosure relates to a method for synthesizing silica nanoparticles, said method comprising the mixing of at least one silane which is negatively charged at physiological pH with
- at least one silane which is neutral at physiological pH, and/or
- at least one silane which is positively charged at physiological pH,
wherein:
- the molar ratio A of neutral silane(s) to negatively charged silane(s) is defined as follows: $0 \leq A \leq 6$, preferably $0.5 \leq A \leq 2$;
- the molar ratio B of positively charged silane(s) to negatively charged silane(s) is defined as follows: $0 \leq B \leq 5$, preferably $0.25 \leq B \leq 3$;
- the molar ratio C of neutral and positively charged silanes to negatively charged silane(s) is defined as follows: $0 < C \leq 8$, preferably $1 \leq C \leq 4$.

As used herein the term "silica nanoparticles" refers to nanoparticles derived from the polymerization of silane precursors. Preferably, said nanoparticles comprise polyorganosiloxane. Said nanoparticles may further comprise additional compounds, including organic molecules. Specific embodiments of the silica nanoparticles as obtained by the method are described hereafter.

As used herein, the term "physiological pH" is considered to be 7.4.

As used herein, the term "silane" refers to compounds having 4 substituents on a silicon atom. In preferred embodiments, the silanes are chosen among alkoxysilanes, hydroxysilanes, and mixture thereof. Examples of silanes that can be used in the method are tetraethyl orthosilicate (Si$(OC_2H_2)_4$, also known as TEOS), tetramethyl orthosilicate (Si$(OCH_3)_4$, also known as TMOS), aminopropyltriethoxysilane (H$_2$N(CH$_2$)$_3$—Si(OC$_2$H$_3$)$_3$, also known as APTES), APTES-DOTAGA, N-(trimethoxysilylpropyl)ethylenediamine triacetic acid, trisodium salt ((CH$_3$O)$_3$Si—(CH$_2$)$_3$N(CH$_2$COONa)(CH$_2$)$_2$N(CH$_2$COONa)$_2$, also known as TANED) and carboxyethylsilanetriol, sodium salt ((HO)$_3$Si—(CH$_2$)$_2$COONa, also known as CEST). As used herein, the term silane also includes any silane compounds that contain chelated metallic cations. As used herein, the term silane also includes any silane compounds resulting from the covalent grafting of any functionalizing agent as described below to a silane precursor; functionalizing agents including for example fluorophores, drugs, organic polymers or targeting ligands.

As used herein, the term "alkoxysilane" refers to compounds of formula (I):

$$R_a Si(OR_i)_{4-n} \qquad (1)$$

wherein:
R is an organyl group;
$R_i$ is a $C_1$-$C_{12}$ alkyl group, preferably a $C_1$-$C_6$ alkyl group;
n is 0, 1, 2 or 3.
According to an embodiment, n is 0 or 1.
As used herein, the term "hydroxysilanes" refers to compounds of formula (II):

$$R_a Si(OH)_{4-n} \qquad (II)$$

wherein:
R is an organyl group;
n is 0, 1, 2 or 3.
According to an embodiment, n is 0 or 1.

As used herein, the terms "organyl group" refer to an organic substituent group, regardless of functional type, linked to the silicon atom via a Si—C bond. Examples of organic substituent group includes without limitation alkylamine.

As used herein, the term "$C_1$-$C_{12}$ alkyl" refers to a linear or branched alkyl functional group having 1 to 12 carbon atoms. Suitable alkyl groups include methyl, ethyl, n-propyl, i-propyl, n-butyl, i-butyl, s-butyl and t-butyl, pentyl and its isomers (e.g. n-pentyl, iso-pentyl), and hexyl and its isomers (e.g. n-hexyl, iso-hexyl).

According to a specific embodiment of the method, the nanoparticles have a mean hydrodynamic diameter of between 0.5 and 15 nm, preferably between 0.5 and 10 nm.

In specific embodiments of the method, the silanes (for example chosen among alkoxysilanes, hydroxysilanes, and mixture thereof) may represent at least 80%, 85% or 90% by weight of the total weight of the reagents, the reagents being the starting compounds used in the reaction for the synthesis of the nanoparticles.

The reaction can be performed in a protic solvent, like alcohols or aqueous solutions. In one particular embodiment, only water is used as a solvent for the reaction. In other embodiments, the reaction is performed in an alcohol or a mixture of alcohols. Alcohols that can be used in the method include ethanol, n-propanol, iso-propanol, n-butanol, tert-butanol, n-pentanol, ethylene glycol and diethylene glycol.

The reaction is preferably performed in a colloidal solution. This enables a better control of the diameter of the nanoparticles. Typically, the reaction is not performed via a classical sol-gel process, to avoid 3 interconnected gel formations.

One advantage of the present method as opposed to prior art method is that it can be performed as a one-pot synthesis, i.e. without any isolation or purification step of the intermediate product(s).

Another advantage is that the design of the specific ratios A, B and C enables the control of the surface charges and the size of the silica nanoparticles, especially, for the production of stable nanoparticles with an average hydrodynamic diameter comprised between 0.5 and 15 nm. In particular, to reduce the size of the nanoparticle below 10 nm, it is preferred to have a ratio A, for example, below 2, and more preferably below 1.5.

According to an embodiment of the method, said negatively charged silane(s) includes or essentially consists of silane(s) comprising at least one, two, or more negatively charged carboxylic acid functions. Examples of negatively charged silanes with carboxylic acid functions includes without limitation: N-(trimethoxysilylpropyl)ethylenediamine triacetic acid, trisodium salt ((CH$_3$O)$_3$Si—(CH$_2$)$_3$N(CH$_2$COONa)(CH$_2$)$_2$N(CH$_2$COONa)$_2$, also known as TANED) and carboxyethylsilanetriol, sodium salt ((HO)$_3$Si—(CH$_2$)$_2$COONa, also known as CEST).

According to another embodiment of the method, said negatively charged silane(s) includes or essentially consists of silane(s) comprising at least one chelating agent. The chelating agent can bear negative charge(s), for example carboxylic acid function(s).

The chelating agent may contain some chelated metallic cations.

The chelating agent may be selected from polyamino polycarboxylic acids including, without limitation:
DOTA (1,4,7,10-tetraazacyclododecane-N,N',N'',N'''-tetraacetic acid), DOTAGA (2-(4,7,10-tris(carboxymethyl)-1,4,7,10-tetraazacyclododecan-1-yl)pentanedioic acid), DO3A-pyridine of formula (III) below:

(III)

DTPA (diethylenetriaminepentaacetic acid), CHX-DTPA (trans-cyclohexyl-diethylenetriaminepentaacetic acid), oxo-Do3A (1-oxa-4,7,10-triazacyclododecane-4,7,10-triacetic acid), SCN-Bz-DTPA (p-isothiocyanatobenzyl-DTPA), 1 B3M (1-(p-isothiocyanatobenzyl)-3-methyl-DTPA), MX-DTPA (1-(2)-methyl-4-isocyanatobenzyl-DTPA);
EDTA (2,2',2'',2'''-(ethane-1,2-diyldinitrilo)tetraacetic acid);
EGTA (ethylene glycol-bis(2-aminoethylether)-N,N,N',N'-tetraacetic acid), BAPTA (1,2-bis(o-aminophenoxy)ethane-N,N,N',N'-tetraacetic acid);

NOTA (1,4,7-triazacyclononane-1,4,7-triacetic acid);
PCTA (3,6,9,15-tetraazabicyclo[9.3.1.]pentadeca-1(15),11,13-triene-3,6,9-triacetic acid);
TMPAC of formula (IV) below:

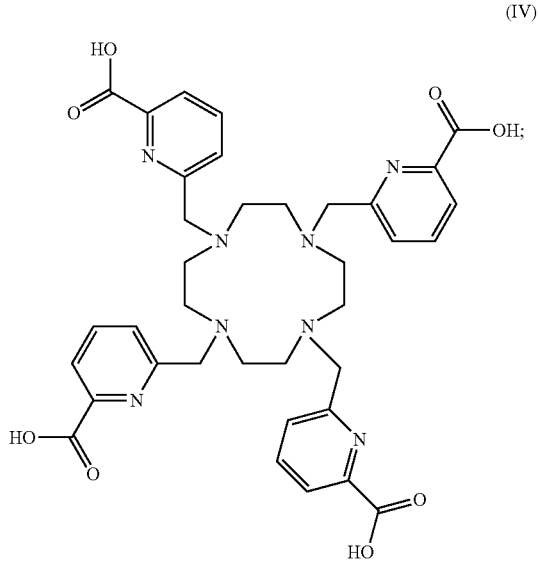

(IV)

and mixtures thereof.

According to an embodiment of the method, the mixing step may further include a silane which is neutral at physiological pH, said neutral silane may comprise a chelating agent. The chelating agent comprised in neutral silane may be chosen for example among porphyrin, chlorine, 1,10-phenanthroline, bipyridine and terpyridine.

According to an embodiment of the method, the nanoparticles as obtained by the method comprise more than 0.1 µmol/mg of chelating agent. For example, the nanoparticles as obtained by the method can comprise more than 0.5 µmot/mg of chelating agent, or between 0.1 and 5 µmol/mg of chelating agent, or between 0.5 and 2 µmol/mg of chelating agent.

According to a particular embodiment of the method, the method includes the use of silanes with chelating agent(s) which is(are) free of metallic ions. For example, less than 5 mol %, 1 mol % or 0.1 mol % of the total chelating agents of the reagents form a complex with metallic ions. In this case, the nanoparticles with free chelating agents as obtained by the method can be chelated in a second step by the metallic ions of interest, depending on the desired application.

Alternatively, the method includes the use of silanes with chelating agent(s) which is(are) chelating a metallic ion. For example, more than 50 mol %, 70 mol % or 90 mol % of the total chelating agents of the reagents form a complex with metallic ions. In this case, the nanoparticles as obtained by the method have chelated metallic ions and can be used directly without further addition of metallic ions.

Metallic ions which can be chelated by the chelating agents include alkali metal ions and their radioactive isotopes, transition metal ions and their radioactive isotopes, post-transition metal ions and their radioactive isotopes, rare earth metal ions and their radioactive isotopes, and mixtures thereof.

Transition metals include Hf, Cu, Pt, Au, Tc, Y, Mn, Ru, Fe, Zr, and mixtures thereof.

Post-transition metals include Bi, Ga, In and mixtures thereof.

Rare earth metals include lanthanides such as Gd, Dy, Eu, Tb, Nd, Yb, Er, Ho, Lu or a mixtures thereof, and more preferably Gd. Radionuclide will for example be chosen from Ac, Th, Pa, Np, U and Pu.

Gd, Dy, Mn and Fe are suitable, for example, for producing nanoparticles that are of use as a contrast agent in MRI.

Eu, Tb, Nd, Yb and Er are suitable, for example, for nanoparticles that are of use as a fluorescence agent.

Ho, Bi, Y and Lu are suitable, for example, for nanoparticles that are of use as a curie-therapy agent.

Lu, Yb, Gd, Bi, Hf and Ho are suitable, for example, for nanoparticles that are of use as a radiosensitizing agent.

Cu, Ga, Tc, Y, In and Zr are suitable, for example, for nanoparticles that are of use as a probe for scintigraphy.

According to specific embodiments of the method, the nanoparticles as obtained by the method comprise more than 10% by weight of metallic ions compared to the total weight of the nanoparticle, for example more than 15%, or between 10 and 20%. This content can be determined by elemental analysis on the freeze dried powder.

According to specific embodiments of the method, the nanoparticles as obtained by the method comprise more than 0.1 µmol/mg of metallic ions, for example more than 0.25 µmol/mg or between 0.1 and 1.5 µmol/mg.

According to an embodiment, the mixing step comprises at least one positively charged silane, said positively charged silane comprising at least one positively charged amino function. Examples of positively charged silane with amino function includes without limitation: APTES.

In specific embodiments of the method, the synthesis of the nanoparticles results in the generation of a polyorganosiloxane network through the formation of siloxane bridges Si—O—Si. These siloxane bridges are obtained by condensation of hydroxysilanes and loss of water. If alkoxysilanes are used in the method of the present disclosure, the reaction is performed in an aqueous solution in order to hydrolyze first the alkoxysilanes to hydroxysilanes. In this case, the nanoparticles have a polyorganosiloxane matrix.

According to a specific embodiment, the method according to the present disclosure comprises the mixing of at least one hydroxysilane or alkoxysilane which is negatively charged at physiological pH and comprises at least one chelating agent chosen from polyamino polycarboxylic acids with
at least one hydroxysilane or alkoxysilane which is neutral at physiological pH, and/or
at least one hydroxysilane or alkoxysilane which is positively charged at physiological pH and comprises an amino function,
wherein:
the molar ratio A of neutral silane(s) to negatively charged silane(s) is defined as follows: $0 \leq A \leq 6$, preferably $0.5 \leq A \leq 2$;
the molar ratio B of positively charged silane(s) to negatively charged silane(s) is defined as follows: $0 \leq B \leq 5$, preferably $0.25 \leq B \leq 3$;
the molar ratio C of neutral and positively charged silanes to negatively charged silane(s) is defined as follows $0 < C \leq 8$, preferably $1 \leq C \leq 4$.

According to a specific embodiment, the method according to the present disclosure comprises the mixing of at least one alkoxysilane which is negatively charged at physiological pH, said alkoxysilane being chosen among APTES-DOTAGA, TANED, CEST and mixtures thereof, with
at least alkoxysilane which is neutral at physiological pH, said alkoxysilane being chosen among TMOS, TEOS and mixtures thereof, and/or
APTES which is positively charged at physiological pH,
wherein:
the molar ratio A of neutral silane(s) to negatively charged silane(s) is defined as follows: $0 \leq A \leq 6$, preferably $0.5 \leq A \leq 2$;
the molar ratio B of positively charged silane(s) to negatively charged silane(s) is defined as follows: $0 \leq B \leq 5$, preferably $0.25 \leq B \leq 3$;
the molar ratio C of neutral and positively charged silanes to negatively charged silane(s) is defined as follows $0 < C \leq 8$, preferably $1 \leq C \leq 4$.

According to a specific embodiment, the method according to the present disclosure comprises the mixing of APTES-DOTAGA which is negatively charged at physiological pH with
at least one alkoxysilane which is neutral at physiological pH, said alkoxysilane being chosen among TMOS, TEOS and mixtures thereof, and/or
APTES which is positively charged at physiological pH,
wherein:
the molar ratio A of neutral silane(s) to negatively charged silane(s) is defined as follows: $0 \leq A \leq 6$, preferably $0.5 \leq A \leq 2$;
the molar ratio B of positively charged silane(s) to negatively charged silane(s) is defined as follows: $0 \leq B \leq 5$, preferably $0.25 \leq B \leq 3$;
the molar ratio C of neutral and positively charged silanes to negatively charged silane(s) is defined as follows $0 < C \leq 8$, preferably $1 \leq C \leq 4$.

Functionalizing Agent

The nanoparticles as obtained by the method may be advantageously functionalized with particular organic molecules, for example for specific medical applications in therapy or imaging.

Accordingly, in particular embodiments of the method, the mixing step may be performed with at least one silane comprising at least one functionalizing agent.

As used herein, the term "functionalizing agent" refers to organic molecules attached to the silanes through covalent conjugation for particular functionalization of the obtained nanoparticles. Such functionalizing agent includes without limitation, fluorophores, drugs, organic polymers or targeting ligands.

Accordingly, in specific embodiments of the method, the mixing step may be performed with at least one silane comprising at least one fluorophore. Preferably, the molar ratio D of silane(s) comprising a fluorophore to neutral silane(s) is defined as follows: $0.001 \leq D \leq 0.2$.

Such silane comprising fluorophore may be obtained by covalent conjugation of a fluorescent compound with reactive moieties to a silica precursor to obtain a fluorescent silica precursor and then reacting the fluorescent silica precursor with a silane, such as tetraalkoxysilane, top form the silane comprising at least one fluorophore. Fluorescent compounds that may be used include without limitation Cy5, Cy5.5, Cy7, fluorescein isothiocyanate (FITC), tetramethylthodamine isothiocynate, X-rhodamine, Alexa, bodipy fluorescent dyes, CW800 and indocyanine green (ICG).

According to another embodiment, the mixing step comprises at least one silane comprising at least one drug moiety. Preferably, the molar ratio E of silane(s) comprising a drug to neutral silane(s) is defined as follows: $0.1 \leq E \leq 5$. According to a specific embodiment, the nanoparticles comprise between 0.5 and 50% by weight of drug moiety compare to the total weight of the nanoparticle, for example between 2 and 10%.

Such silane comprising drug moiety may also be obtained by first preparing a linker-drug moiety, for example as described in the literature for antibody-drug-conjugates and then reacting by covalent conjugation the linker-drug moiety to at least one silane to form said silane comprising at least one drug moiety. Examples of linkers include the cleavable linkers such as para-aminobenzyloxycarbonyl (PABC) group.

Examples of drugs which can be used to prepare the silane containing drug moiety include without limitation small molecule drugs and for example, chemotherapeutic drugs such as alkylating agents, anthracyclines, taxanes, HDAC inhibitors, inhibitors of topoisomerase I or II, kinase inhibitors, nucleoitide analogues and precursor analogues. Specific examples of drugs which can be used to prepare the silane containing drug moiety include without limitation actinomycine, acide rétinoique all-trans, azacitidine, azathioprine, bléomycine, bortezomib, carboplatine, capecitabine, cisplatine, chlorambucil, cyclophosphamide, cytarabine, daunorubicine, docetaxel, doxifluridine, doxorubicine, epirubicine, epothilone, etoposide, fluorouracil, gemcitabine, hydroxyureal, darubicine, imatinib, irinotecane, mechlorethamine, mercaptopurine, methotrexate, mitoxantrone, oxaliplatine, paclitaxel, pemetrexed, teniposide, tioguanine, topotecan, valrubicin, vemurafenib, vinblastine, vincristine, vindesine. lenalidomide, ibrutinib, abiratérone, erlotinib, everolimus, nilotinib, sunitinib, sorafénib, goserelin, nedaplatine, laboplatine, heptaplatine, and mixtures thereof, According to another embodiment, the mixing step comprises at least one silane comprising at least one targeting ligand.

As used herein, the targeting ligand is a molecule attached to the silane that contributes to targeting the nanoparticles in vivo to specific cellular components. Such ligand can target a specific organ, tissue or cell type in vivo, for example for specific medical or diagnostic applications.

Such targeting ligand may be for example a peptide, a protein, a sugar (e.g. lectin), a biopolymer, a synthetic polymer, an antigen, an antibody, an aptamer and a nanobody. Example of targeting ligands, include without limitation, Herceptin (Trastuzumab), Rituxan (Rituximab), CD 19 antibody, pepaptanib, A10 aptamer, cRGD peptide, ATWLPPR peptide, VAP, Lyp-1, transferrin, LFRH, folic acid, galactose, or ASGPR targeting ligands, biotin, mannose According to another embodiment, the mixing step comprises at least one silane comprising at least one organic polymer.

Such organic polymers may be for example PEG (polyethyleneglycol), polylactate, polylactic acids, sugards, lipids, polyglumatic acid (PGA), polyglycolic acid, poly(lactic-co-glycolic acid) (PLGA), polyvinyl acetate (PVA) and the combinations thereof.

It has been shown that contrary to prior art method, the present method enables to produce ultrasmall and stable nanoparticles without the need to use stabilizing organic polymers. Therefore, in one specific embodiment, the method of the present disclosure does not include any organic polymers grafted to the silanes.

Silica Nanoparticles

The invention also relates to a silica nanoparticle as obtained by the method as described above.

Typically, the silica nanoparticles obtained by the method have advantageously a mean hydrodynamic diameter between 0.5 and 15 nm, for example between 1 and 10 nm, or between 1 and 5 nm, or between 2 and 7 nm. The skilled person will be able according to the teaching of the present disclosure to adapt the specific ratios A, B and C as defined in the method to obtained the desired size of the silica nanoparticles.

As used herein, the term "mean hydrodynamic diameter" is intended to mean the harmonic mean of the hydrodynamic diameters of the particles. A method for measuring this parameter is by photon correlation spectroscopy, which method is also described in standard ISO 13321:1996.

The silica nanoparticles as obtained by the method may further comprise a fluorescent compounds, a chelating agent (with or without metal), a drug moiety, a targeting ligand, or organic polymers covalently attached. In specific embodiments, such silica nanoparticles as obtained by the method have either Eu, Cu, Gd, Tb, Ho, Bi, or mixtures thereof as metallic ions chelated by the chelating agent. In a specific embodiment, such silica nanoparticles as obtained by the method have Gd as metallic ions chelated by the chelating agent. In specific embodiments, such silica nanoparticles as obtained by the method have Bi, Hf, or mixtures thereof as metallic ions chelated by the chelating agent. In specific embodiments, such silica nanoparticles as obtained by the method have Lu, Y, Cu Zr, In, Ga, or mixtures thereof as metallic ions chelated by the chelating agent. In specific embodiments, such silica nanoparticles as obtained by the method have rare earth metal ions as metallic ions chelated by the chelating agent.

In specific embodiments, the nanoparticles as obtained by the method do not comprise a crystalline core, as can be found for example in nanoparticles with core-shell structures. For example, the nanoparticles as obtained by the present method do not comprise a crystalline core of metals, oxides, sulfides, fluorides or carbides.

In one embodiment of the invention, the nanoparticles do not comprise a metallic core, such as Gd oxide core, whether crystalline or not. According to an embodiment, the silica nanoparticles do not comprise a polyethylene glycol (PEG) shell.

The disclosure also relates to a silica nanoparticle having a mean hydrodynamic diameter of between 0.5 and 15 nm comprising a polyorganosiloxane matrix which is grafted with chelating agents, said chelating agents being free of metallic ions and present at a content of at least 0.1 µmol/mg of nanoparticle, preferably between 0.5 and 2 µmol/mg. For example, in one specific embodiment, the chelating agent is DOTAGA and the content of the chelating agent is comprised between 0.5 and 2.

The content of chelating agents free from metallic ions can be determined by HPLC, or by titration for example directly with europium or with gadolinium in combination with xylenol orange.

Use of the Silica Nanoparticles

The nanoparticles according to the present disclosure can be preferably used in therapy or diagnostic methods or as a theranostic agent.

For example, the nanoparticles may be used as therapeutic agent, such as a sensitizer or radioactive sources for radiotherapy or neutron therapy, agent for photodynamic therapy (PDT), or a delivery agent for therapeutic molecules (such as chemotherapeutic agent).

The nanoparticles may also be advantageously used as a multimodal imaging agent, which can act as contrast agent in magnetic resonance imaging (MRI), or in scintigraphy with single photon emission computed tomography (SPECT) or positron emission tomography (PET), or in optical imaging by fluorescence, or in X-ray computed tomography (X-ray CT) or in a multimodal imaging which combines at least two of those techniques.

The nanoparticles with free chelating agents may further be used as a chelator of toxic metals in the body, for example chelator of Hg, Pb, Al, Cd or Cr.

The nanoparticles with free chelating agents may further be used to regulate metal homeostasis, especially to regulate endogenous metals, like Fe, Cu, Zn, or Mn, or to regulate exogenous metals, like Hg, Pb, Al, Cd or Cr.

The present disclosure thus relates to a pharmaceutical composition comprising a therapeutically efficient amount of the silica nanoparticles as obtained by the above defined method in combination with a pharmaceutically acceptable vehicle.

The present disclosure further relates to a method of imaging in human or animal, comprising the following steps:
  (i) administering the nanoparticles as obtained by the present disclosure, as T1 MRI contrast agent,
  (ii) capturing images using an appropriate MRI sequence.

The present disclosure further relates to a method of treating a patient in need thereof by radiotherapy, comprising the following steps:
  (i) administering the nanoparticles as obtained by the present disclosure, as a sensitizer for radiotherapy,
  (ii) irradiating the patient for radiotherapy.

For such specific application, the nanoparticles of the present disclosure, preferably includes Gd as radiosensitizers chelated to chelating agents.

BRIEF DESCRIPTION OF THE DRAWINGS

FIG. 6 shows the reaction scheme of the synthesis of APTES-DOTAGA according to example 2, step 1.a.

FIG. 11 shows the titration curve of UCHSNP sample at 594 nm (circles) and 616 nm (squares) excited at 395 nm according to example 2, step 2.a.

FIG. 12 shows the NMR spectra of UCHSNP-1: NMR-DOSY spectrum (FIG. 12A); $^1$H NMR spectrum of UCHSNP-1 at 127 gel (FIG. 12B); NMR-DOSY spectrum (FIG. 12C); $^1$H NMR spectrum of UCHSNP-1 @Lu at 127 g/l (FIG. 12D) and the positions of H1, H2 and H3 on the APTES and APTES-DOTAGA functional groups on the particle (FIG. 12E) according to example 2, step 2.a.

FIG. 21 shows the DLS diagrams of UCHSNP-7 at different step during the synthesis: APTES+DOTAGA anhydride in DEG (dotted line, squares), APTES+DOTAGA anhydride+TEOS in DEG (dotted line, up triangles), APTES+DOTAGA+TEOS in $H_2O$ (dotted line, down triangles), APTES+DOTAGA+TEOS in $H_2O$ filtered through 0.2 μm membrane (straight line, circles) (FIG. 21A); after purification (FIG. 21B) according to example 4.

FIG. 22 shows the Eu titration curve of UCHSNP-7 nanoparticles according to example 4.

EXAMPLES

Figure 1:
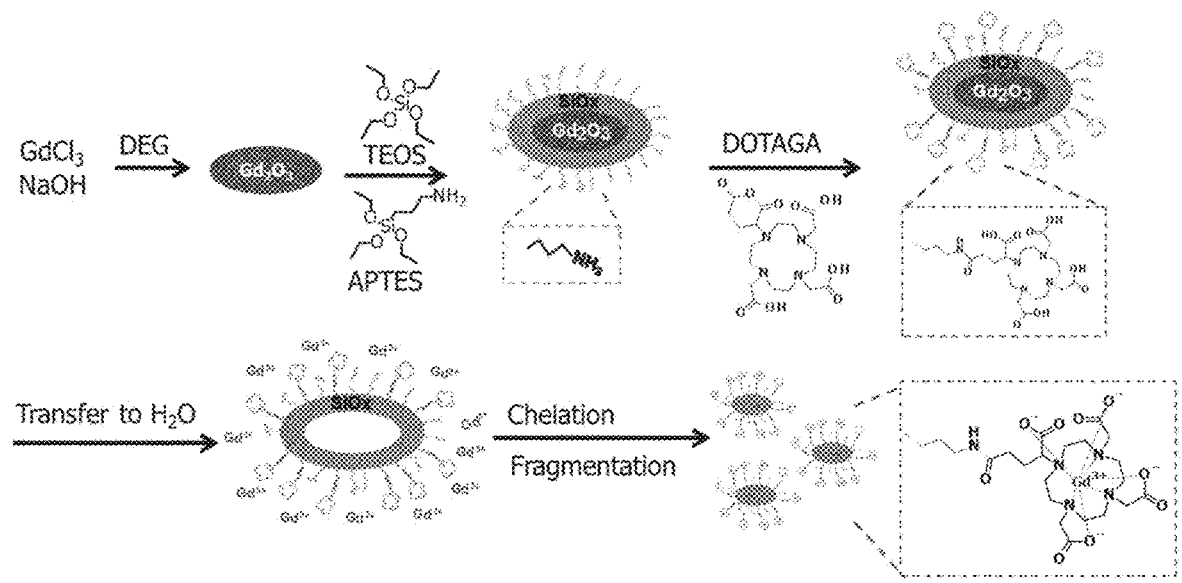
FIG. 1 shows the reaction scheme of the synthesis of nanoparticles as reported in WO2011135101 A2.

Materials and Methods
Materials

Hydrochloric acid (HCl, 37%) were purchased from VWR Chemicals BDH Prolabo (France). Sodium hydroxide pellets (NaOH, ≥98%) were purchased from Sigma-Aldrich Chemicals (France). Solutions of hydrochloric acid and sodium hydroxide in water at different concentrations from 2 M to $10^{-4}$ M were prepared to adjust pH of solutions. Europium chloride hexahydrate ($EuCl_3.6H_2O$, 99.9%), lutetium chloride hexahydrate ($LuCl_3.6H_2O$, 99.9%), terbium chloride hexahydrate ($TbCl_3.6H_2O$, 99.9%), holmium chloride hexahydrate ($HoCl_3.6H_2O$, 99.9%), Tetraethyl orthosilicate ($Si(OC_2H_5)_4$, TEOS, 98%), aminopropyltriethoxysilane ($H_2N(CH_2)_3-Si(OC_2H_5)_3$, APTES, 99%), anhydrous DMSO for the synthesis of the silane precursor, deuterium oxide $D_2O$ for NMR experiments, glacial acetic acid for preparing buffer at pH 5, Eriochrome® Black T (EBT) and ammonia buffer solution at pH 10 for complexometry, were purchased from Sigma-Aldrich Chemicals (France). N-(trimethoxysilylpropyl)ethylenedi amine triacetic acid, trisodium salt $((CH_3O)_3Si-(CH_2)_3N(CH_2COONa)(CH_2)_2N(CH_2COONa)_2$, TANED, 45% in water) and carboxyethylsilanetriol, sodium salt $((HO)_3Si-(CH_2)_2COONa$, CEST, 25% in water) were purchased from ABCR GmbH (Germany). 1,4,7,10-Tetraazacyclododecane-1-glutaric anhydride-4,7,10-triacetic acid (DOTAGA anhydride) was provided by Chematech (France). Gadolinium chloride hexahydrate ($GdCl_3.6H_2O$, 99.999%) was purchased from Metall Rare Earth Limited (China). Milli-Q water (ρ>18 MΩ) was used as water source. Vivaspin® concentrators and Vivaflow® 200 cassettes (MWCO=3 kDa or 5 kDa) were purchased from Sartorius Stedim Biotech (France).
Methods
Dynamic Light Scattering (DLS) and Zeta Potential Hydrodynamic diameter distribution of the nanoparticle was measured by DLS with a Zetasizer Nano-S (633 nm He—Ne laser) from Malvern Instruments. Measurement was taken on 0.5-1 ml of the solution with a single use PMMA cuvette (Carl Roth GmbH, Germany). Attenuator and position were optimized by the device. To determine zeta potential, lyophilized powder was redispersed in water to achieve 100 mg/ml solution and diluted to 10-18 mg/ml in an aqueous solution containing 5 mM NaCl and adjusted to the desired pH just before each measurement. Zeta potential measurements were recorded at 20° C. within a DTS 1061 folded capillary cell (Malvern Instruments Ltd, USA). The zeta potential (ζ) was automatically calculated from electrophoretic mobility based on the Smoluchowski equation, $v=(\varepsilon\varepsilon_0\zeta/\eta)\zeta$, where v is the measured electrophoretic mobility, η is the viscosity, ε is the dielectric constant of the electrolytic solution, $\varepsilon_0$ $8.854\times10^{-12}$ $C^2N^{-1}m^{-2}$ is the vacuum permittivity. Lyophilized powder was redispersed in water to achieve 100 mg/mL solution and diluted to 10 mg/mL in an aqueous solution containing 5 mM NaCl and adjusted to the desired pH just before each measurement.
Chromatography
Method 1: Determination of the Purity of Nanoparticles and to Quantify the Free DOTAGA on Nanoparticles Gradient HPLC analysis was done by using the Shimadzu Prominence series UFLC system with a CBM-20A controller bus module, a LC-20AD pump, a CTO-20A column oven, and a SPD-20A UV-vis detector. The detecting wavelength was set at 295 nm where only organic chelators can highly absorb for characterizing empty nanoparticles or at 700 nm where copper complex of DOTAGA specifically absorb for characterizing copper incorporated nanoparticles. A FR-20A Fluorescence detector ($\lambda_{ex}$=274 nm, $\lambda_{em}$=312 nm) was added to detect the fluorescence signal from Gd complexes when characterizing gadolinium incorporated nanoparticles. The column temperature was maintained at 30° C. Gradient LC elution was carried out with two mobile phases: (A) Milli-Q water/TFA 99.9:0.1 v/v and (B) acetonitrile ($CH_3CN$)/TFA 99.9:0.1 v/v. Each time, an amount of 20 μL of sample was loaded to an injection valve and injected into a Jupiter C4 column (150 mm×4.60 mm, 5 μm, 300 Å, Phenomenex) at a flow rate of 1 mL/min. Then the elution was programmed as follows: 1% of solvent B in 7 min to elute the reactive and fragments, then a gradient from 1% to 90% in 15 min to elute the nanoparticle. The concentration of B was maintained over 7 min. Then, the concentration of solvent B was decreased to 1% over 1 min and maintained during 8 min to re-equilibrate the system for a new analysis. Before the measurement of each sample, a baseline was obtained under the same conditions by injecting Milli-Q water. The purity is calculated by dividing the area under the peak of the particle to the total area under the peaks of the particle and the reactive. This method was also used to quantify the content of free DOTAGA on nanoparticles using $Cu^{2+}$ as probe. An excess of $CuSO_4$ was added to a solution of ultrasmall hybrid chelating silica nanoparticle (UCHSNP) whose pH has been already adjusted less than or equal to 3. The complexation could probably reduce the pH of the solution. Therefore, pH should be readjusted to be stable at 3 before being incubated at 80° C. for at least 2 h. Visible detector at 700 nm was used to detect specifically the absorption of copper complexes which are free or grafted on the nanoparticles. The concentration of $Cu^{2+}$ and DOTAGA ($Cu^{2+}$) was determined by comparing peak area with their calibration curves at different concentrations (4 mM-32 mM for $Cu^{2+}$ and 0.1 mM-15 mM for DOTAGA($Cu^{2+}$)). The total concentration of free $Cu^{2+}$ and DOTAGA($Cu^{2+}$) can be summed up to verify with the introduced amount. The content (mol/g) of free DOTAGA can be calculated from their molar concentrations (mol/L) and the mass concentration (mg/L) of the analyzed samples.
Method 2: Identification of APTES-DOTAGA after its Synthesis from DOTAGA Anhydride Isocratic HPLC analysis was done by using the same system as described in method 1. The fluorescence detector ($\lambda_{ex}$=274 nm, $\lambda_{em}$=312 nm) was the main detector in this case to detect the signal from Gd complexes. The mobile phase is fixed at 100% (A) and 0% (B) to slow down the elution of $Gd^{3+}$, APTES-DOTAGA($Gd^{3+}$) and DOTAGA ($Gd^{3+}$) as well as to clearly separate them. The samples were introduced in the same manner as method 1. The flow was maintained for 10 min to elute all the expected peaks. After that, solvent B was raised to 100% gradually to wash accumulated impurities in the samples or in the solvents from the column. Then, the concentration of solvent B was decreased to 0% over 1 min and maintained during 15 min to re-equilibrate the system for a new analysis. Before the measurement of each sample, a baseline was obtained in the same manner as the former method. The product of the synthesis was dissolved in water and mixed with $GdCl_3$ to achieve final concentration of 5 g/l and 10 mM for the synthesis mixture and $Gd^{3+}$ respectively at pH around 6 and incubated at 37° C. during 15 h to allow the complexation.

After the analysis, the elute was collected for studying by mass spectrometry (MS). The eluted solution was lyophilized to remove solvents and the excess of TFA. The lyophilized powder was redispersed in water at a concentration double higher than before lyophilization to make sure the sample is enough concentrated for MS analysis. A sample of $GdCl_3$ 10 mM at pH 6 and a mixture of DOTAGA ($Gd^{3+}$) 2 mM plus $GdCl_3$ 1 mM at pH 5 were analyzed in the same condition with HPLC to identify the peak of $Gd^{3+}$ and DOTAGA($Gd^{3+}$) through retention time ($t_R$).

Method 3: Quantification of the Amount of Silane Precursor APTES DOTAGA after its Synthesis from DOTAGA Anhydride Isocratic HPLC analysis was done by using the same system and setting for fluorescence detector as in method 2. The samples were introduced in the same manner. However, a BDS-HYPERSIL-C18 column (250 mm×4.60 mm, 5 μm, ThermoFisher Scientific) was used instead of C4 column to increase the separation capacity for small molecules. Moreover, the mobile phase is fixed at 99% (A) and 1% (B) instead of 100% of (A) to avoid the slight fluctuation of the $t_R$ of the peaks. The latter is due to the "hydrophobic collapse" because the solvent is not hydrophobic enough to wet the surface of the static phase. The flow was maintained for 25 min to elute all the expected peaks. After that, solvent B was raised to 100% gradually for the same purpose as above. Then, the system was re-equilibrated before a new analysis. Before the measurement of each sample, a baseline was obtained in the same manner. The product of the synthesis was dissolved in acetate buffer pH 5. To this solution, solution of $GdCl_3$ 50 mM at pH 4 was added to achieve final concentrations of 57.8 mg/L and 0.2 mM for the synthesis mixture and $Gd^{3+}$ respectively. This solution was incubated at 80° C. during 48 h to allow the complexation to complete. The final solution was transparent but filtration through 0.2 μm membrane was done to make sure big particles of dust will not block the HPLC column. A sample of $GdCl_3$ 1 mM at pH 4 and a mixture of DOTAGA ($Gd^{3+}$) 0.05 mM at pH 5.7 were analyzed in the same condition to identify the peak of $Gd^{3+}$ and DOTAGA($Gd^{3+}$) through $t_R$. The concentration of DOTAGA($Gd^{3+}$) was determined by comparing its peak area with its calibration curve at different concentrations (0.01 mM-0.15 mM). The concentration of APTES-DOTAGA($Gd^{3+}$) was determined indirectly by subtracting the concentration of DOTAGA ($Gd^{3+}$) from the total concentration of APTES-DOTAGA and DOTAGA determined by the titration using Eu phosphorescence. The content (mol/g) of unreacted DOTAGA and APTES-DOTAGA can be calculated from their molar concentrations (mol/L) and the mass concentration (mg/L) of the analyzed synthesis mixture.

Mass Spectrometry (MS)

MS was used to identify the peaks of APTES-DOTAGA ($Gd^{3+}$) and DOTAGA($Gd^{3+}$) in HPLC chromatogram. Mass spectra were recorded on Time of Flight Mass Spectrometer micrOTOF-Q II (Bruker Daltonics, Germany) in negative mode.

$^1$H Nuclear Magnetic Resonance (NMR) and Diffusion Ordered Spectroscopy (DOSY)

All experiments were performed at 298 K, without spinning, on a Bruker Avance III 500 MHz spectrometer equipped with 5 mm BBFO and BBI probes. Lyophilized silica nanoparticle was dispersed in $D_2O$.

For $^1$H NMR diffusion experiments, the standard ledbpgp2s sequences were used. The diffusion delay d20 were set to 100 ms, and the bipolar pulses p30 were adjusted to obtain a 95% attenuation at full strength, typically in the range of 2 to 4 ms. 32 or 64 points were acquired in the diffusion dimension. Comparing processed data obtained with the standard dosy2d command, the DynamicCenter and NMRnotebook programs, best results were obtained with NMRnotebook, which provided a good fit of data, even when several signals are mixed at the same chemical shift.

The reported hydrodynamic diameters ($D_H$) are simply derived from the diffusion coefficients (D) with the well-known Stokes-Einstein formula: $D_H=kBT/3\pi\eta D$, in which kB is the Boltzmann constant, T the absolute temperature, and η the viscosity of the solvent (1.13 cP for $D_3O$ at 298K).

Solid-State $^{29}$Si NMR Spectroscopy

Solid state $^{29}$Si NMR experiments were performed on a Bruker Avance 500 WB spectrometer, with a MAS 4 mm double H/X probe, at a MAS rate of 10 kHz, spectral frequency at 99.34 MHz. High power decoupling MAS pulse sequence is used to get quantitative spectra with pulse length of 4 μs (corresponding to a 90° pulse), repetition delay 240 s during 1200 acquisition scan. Spectral decomposition was performed by DMFit software. The signal can be de-convoluted into six contributions that correspond to six different Si environments. They are of two main types: $CSi(OSi)_nO_{3-n}$ and $Si(OSi)_mO_{4-m}$, commonly labelled $T_n$ (for tertiary) and $Q_m$ (for quaternary), respectively. $T_n$ species are formed from organotrialkoxysilanes such as CEST, APTES, TANED or APTES-DOTAGA and $Q_m$ from tetraalkoxysilanes such as TEOS.

Titration by Eu Phosphorescence

Titration by Eu phosphorescence is the main method to precisely quantify the content of chelating agent (mol/g) in the synthesis mixture of APTES-DOTAGA and in lyophilized final powders. Synthesis mixture or lyophilized powder was redispersed in water. A series of samples with a certain amount of this solution and an increasing amount of $EuCl_3$ was prepared in acetate buffer pH 5. These series of samples were incubated at 80° C. for 48 h before the measurement. Phosphorescence measurements were carried out using a Varian Cary Eclipse fluorescence spectrophotometer, in the resolved time mode. For single read measurement, parameters were set up as follows: excitation wavelength at 395 nm, emission wavelength at 594 nm and 616 nm, which is the characteristic excitation and emission for $Eu^{3+}$ ions, excitation slit 10 nm, emission slit 10 nm, delay time 0.2 ms, total decay time 0.02 s, averaging time 5 s, gate time 5 ms, number of flash 1, excitation filter 335-620 nm, emission filter 550-1100 nm, high voltage. For scanning the emission spectrum, similar parameters with resolution 1 nm were used except that averaging time was reduced to 1 s to speed up the measurement. The endpoint was determined when the luminescence intensity no longer increased linearly with the added amount of $Eu^{3+}$.

Relaxivity Measurement

Relaxivity measurements were performed on a Bruker® minispec mg60NMR analyzer (Brucker, USA) at 37° C. at 1.4 T (60 MHz). Samples were measured at a specific $Gd^{3+}$ concentration (mM), measured from either CP-OES or elemental analysis. The longitudinal relaxation time $T_1$ and the transverse relaxation time $T_2$ (s) were measured. Then the relativities $r_i$ ($s^{-1} \cdot mM^{-1}$) (i=1, 2) were obtained according to the following formula:

Elemental Analysis

Elemental analysis was conducted by FILAB SAS., Dijon, France and enabled determination of the Gd, C, N and Si contents of the powder samples.

Inductively Coupled Plasma-Optical Emission Spectrometry (ICP-OES)

The determination of the accurate concentration of metals in the nanoparticle was performed by inductively coupled plasma-optical emission spectrometry (ICP-OES) (with a Varian 710-ES spectrometer, USA). The solution after DLS measurement was reused for this measurement. The solution of particles at an estimated concentration in metal (Gd, Tb, Ho or Bi) of 10 ppm was digested for 3 h in 4-5 mL of aqua regia (HNO₃ 67% mixed with HCl 37% (1/2; v/v) at 80° C. Subsequently, the mixture was diluted to estimated 100, 200 and 400 ppb at precisely 50 mL with HNO₃ 5% (v/v). These solutions were filtered through 0.2 μm membrane before being analyzed. Calibrated samples were prepared from 1000 ppm Gd, Tb, Ho and Bi standard solutions by successive dilutions with HNO₃ 5% (w/w). The selected wavelengths for measurement were 342.246, 335.048, 336.224 nm for Gd samples; 350.914, 367.636, 387.417 nm for Tb samples; 345.600, 339.895, 341.644 nm for Ho samples and 223.061 nm for Bi samples. The results were the average of the three samples at presumably 100, 200 and 400 ppb at different selected wavelengths.

UV-Visible Spectroscopy

UV-visible spectra were recorded with Varian Cary 50 spectrophotometer (USA). Solutions of UCHSNP-7 and UCHSNP-7@Ho were measured at 5 g/L; UCHSNP-7, UCHSNP-7@M (M: Gd, Tb, Ho, Bi) at 0.06 g/L.

Infrared Spectroscopy (IR)

Infrared spectra were performed with a IRAffinity-1 Shimadzu. Transmittance mode was used with Happ-Genzel apodization function, 30 scans, 4 cm$^{-1}$ resolution in a range between 400 and 4000 cm$^{-1}$. pHs of the solutions were adjusted to 2 before being lyophilized. The spectra were recorded on the obtained powders.

Example 1: Synthesis of the Ultrasmall Silica Nanoparticle in Water Using TANED, CEST and TEOS TANED (8.22 ml, 8 mmol) and CEST (5.57 ml, 8 mmol) were added in water (63 ml) and stirred at room temperature for 15 minutes. Then TEOS (5.57 ml, 16 mmol) was added to the above solution. It was stirred at room temperature over night to let the solution become homogeneous. After that, pH of solution was decreased from 10.5 to 7.4 by adding few drops of HCl at appropriate concentrations. The solution was left to stir during 24 hours before being re-adjusted from pH 7.4 to pH 4.5. The solution was stirred during 6 hours before being put in an oven and left static at 80° C. for one night. A little solution was filtered through 0.2 μm membrane and analyzed by Dynamic Light Scattering (DLS) and High Performance Liquid Chromatography (HPLC). Then whole solution was purified by filtration through Vivaspin™ (MWCO=3 kDa) with 10$^{-4}$ M HCl solution as solvent. The solution was introduced into 20 mL Vivaspin tubes, and centrifuged until half of the volume remains (purification rate 2'=2). This step was repeated several times, by filling the tubes with hydrochloric acid solution 10$^{-4}$ M and centrifuging again, until the purity calculated from HPLC chromatogram reaches ≥90% (normally, 2$^8$=256 purification rate). Then, the solution was filtered through 0.2 μm membrane to remove the largest impurities. Finally, the solution was freeze dried for long term storage.

Figure 2:
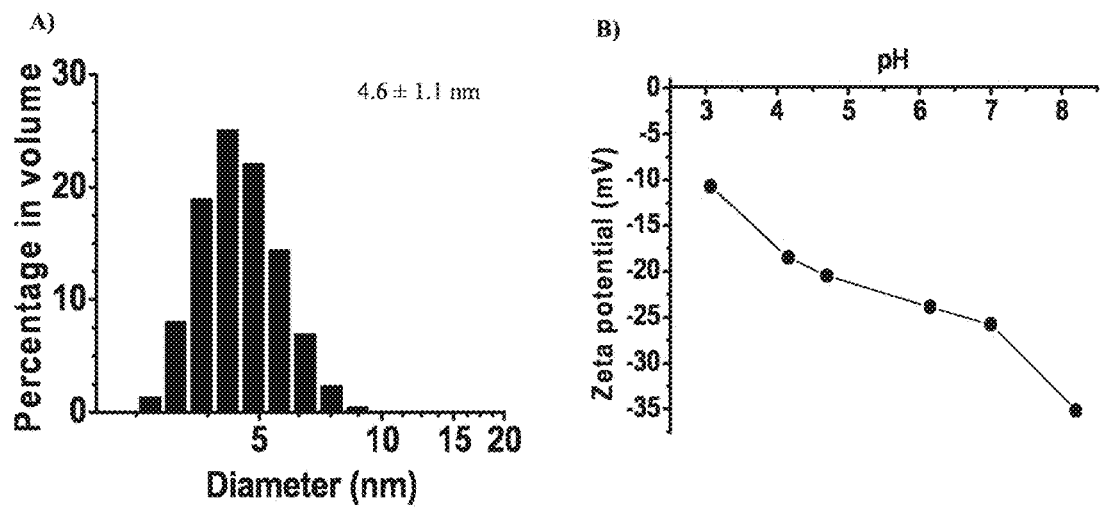
FIG. 2 shows the DLS diagram (FIG. 2A) and zeta potential (FIG. 2B) of the nanoparticles according to example 1.

The obtained particles were characterized in terms of hydrodynamic size, zeta potential and composition. FIG. 2-A shows the size distribution of the final particle measured by DLS. The average size is around 4.6 nm with the standard deviation of 1.1 nm. FIG. 2-B shows the zeta potential in the function of pH measured by laser Doppler velocimetry integrated in the same instrument. The measurement was stopped at pH 8 due to reduced stability of polysiloxane at basic pH. The final particles have negative surface charge as expected. The zeta potential at pH 7 is −25.8 mV.

HPLC analysis was performed according to method 1. The purity of the final nanoparticles based on the absorption at 295 nm is 92.4%.

Figure 3:
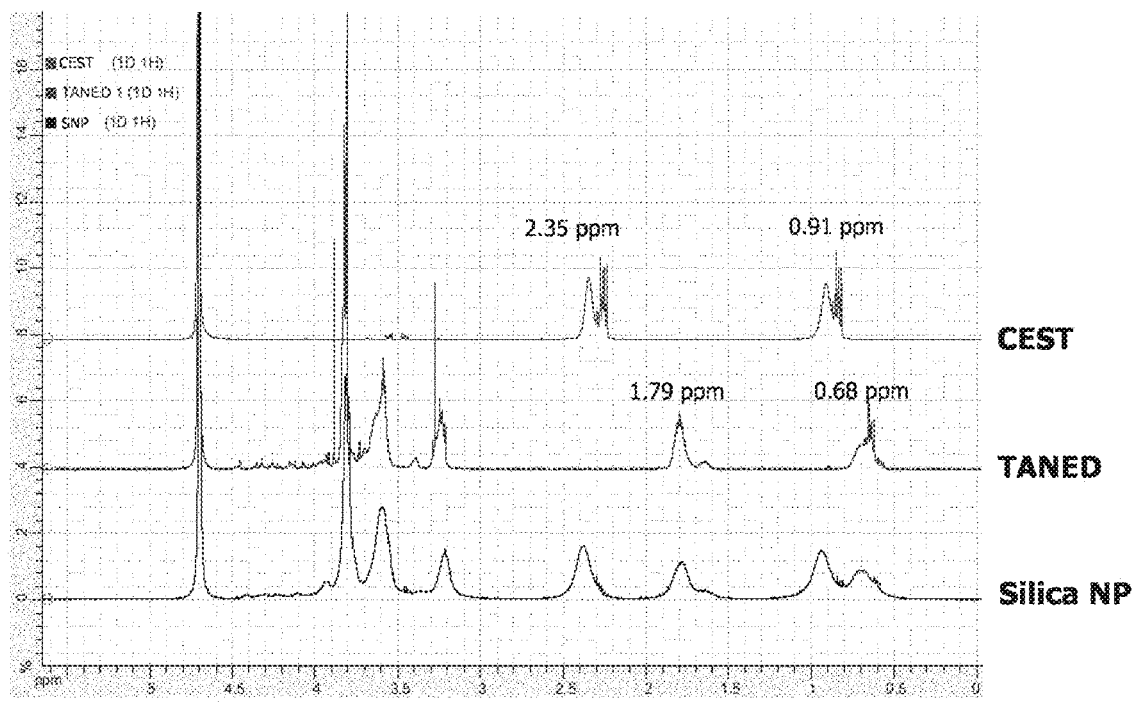
FIG. 3 shows the $^1$H-NMR spectra of CEST, TANED and the nanoparticles according to example 1 in $D_2O$.
Figure 4:
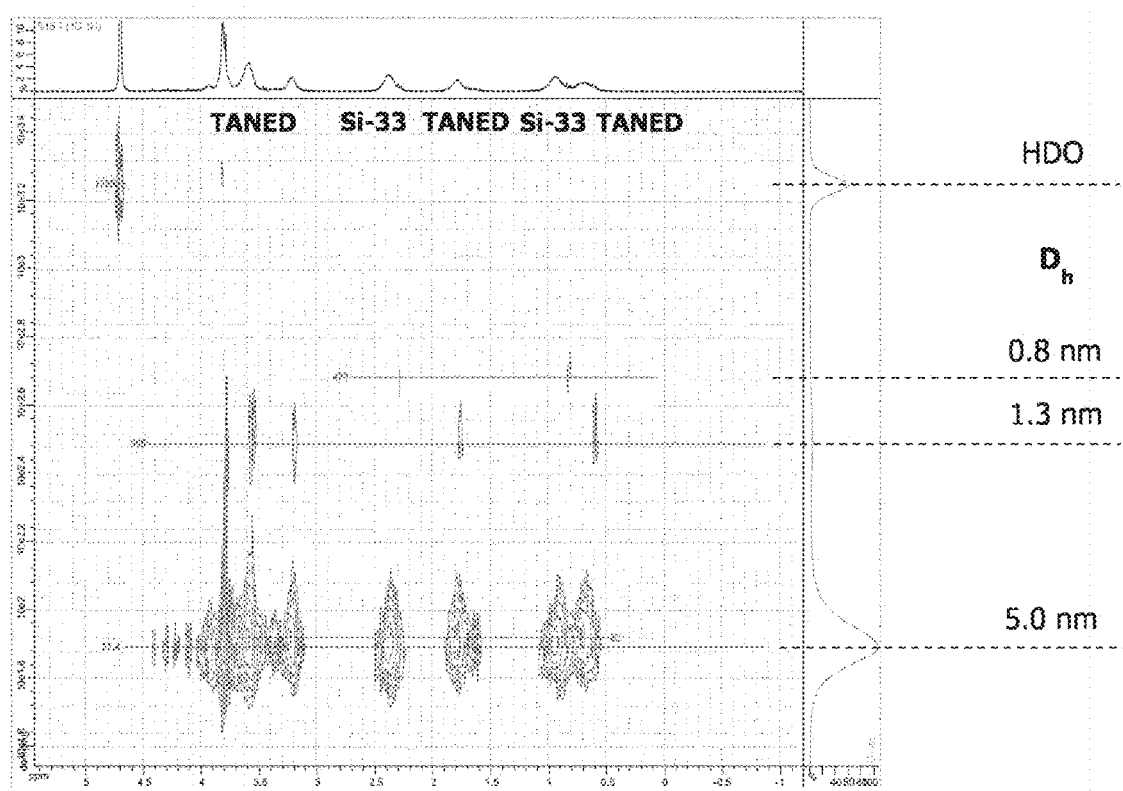
FIG. 4 shows the 2D-NMR (DOSY) spectrum in $D_2O$ of the nanoparticles according to example 1.

FIG. 3 shows the $^1$H nuclear magnetic resonance (NMR) spectra of CEST, TANED and the final nanoparticles in D₂O. This result shows that CEST and TANED are incorporated in the final nanoparticles. FIG. 4 shows a 2D NMR spectrum created by applying diffusion ordered spectroscopy (DOSY) technique on the sample of the final nanoparticles in D₂O. This technique allows us to measure the diffusion coefficient ($D_H$) correlating to each $^1$H signal. In FIG. 4, the x axis shows the chemical shifts (ppm) where all of $^1$H peaks observed previously in 1D $^1$H spectra were found. The y axis shows the value of $D_H$. Then, from the diffusion coefficients, we can calculate the hydrodynamic diameter of the species which give these $^1$H peaks. There are 3 values of $D_H$ which can be assigned to the one from the nanoparticles and two types of free hydrolyzed silanes. So, some conclusions can be made from the spectrum. First, two expected functional groups have been well grafted on the particles. Second, the purified particles have stable grafted functions with very few free hydrolyzed silanes. Finally, the hydrodynamic diameter of the particle is approximately 5.0 nm which is in accordance with the result measured from DLS.

Figure 5:
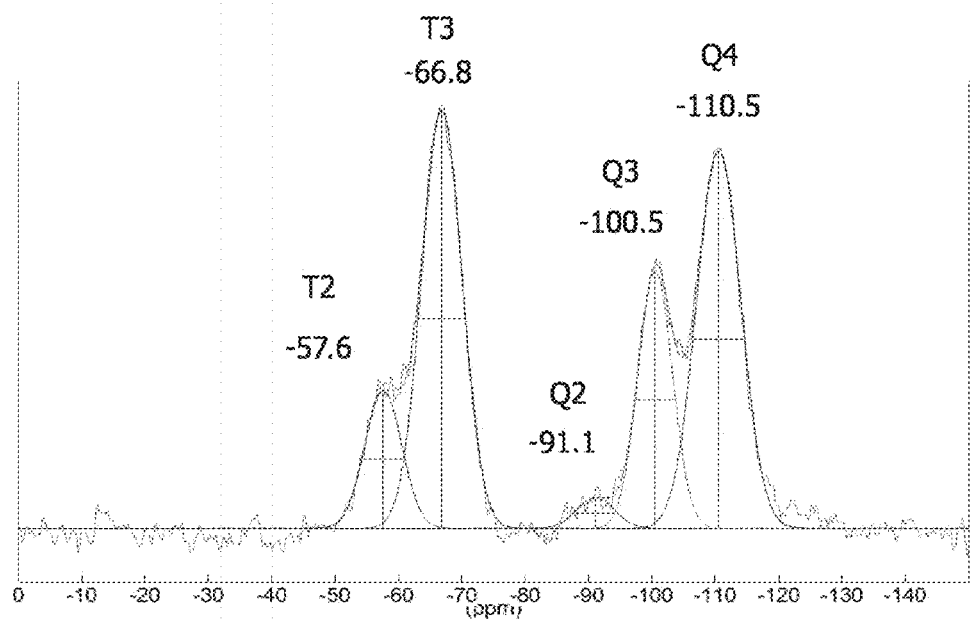
FIG. 5 shows the solid state $^{29}$Si-NMR spectrum of the nanoparticles according to example 1.

By comparing the areas of $^1$H peaks coming only from CEST with the total area of all $^1$H peak which come from both CEST and TANED, the ratio between the amount of CEST and the amount of TANED in the sample can be calculated. In this example, the result was CEST/TANED=1.30. Table 1 and FIG. 5 show the result from solid state $^{29}$Si NMR spectroscopy. First of all, 45% of the Si ($T_2$ and $T_3$) is from the organosilanes, i.e. TANED and CEST. By combining this value with the result obtained from the comparison of the the areas of $^1$H peaks, we can calculate that 25.45% are from CEST and 19.55% from TANED. Then the remaining 55% of Si ($Q_2$, $Q_3$ and $Q_4$) comes from TEOS.

TABLE 1

| Species | Amplitude | Position (ppm) | Width (Hz) | Peak area (%) | Absolute area |
|---|---|---|---|---|---|
| $T_2$ | 3.66 | −57.6 | 679.7 | 10.5 | 2646 |
| $T_3$ | 11.11 | −66.8 | 740.8 | 34.7 | 8764 |
| $Q_2$ | 0.81 | −91.1 | 693.1 | 2.4 | 595 |
| $Q_3$ | 6.84 | −100.5 | 634.1 | 18.3 | 4617 |
| $Q_4$ | 10.03 | −110.5 | 812.0 | 34.3 | 8668 |

From the above results we can establish the molar ratio of all compositions as following TANED:CEST:TEOS=1.00:1.30:2.81. Besides, we can also calculate the content of TANED from this ratio which is around 0.784 μcool/mg.

The content of TANED can also be quantified by colorimetry with EBT (or NET) as the color indicator. Lyophilized powder was redispersed in water to achieve 48 mg/ml solution (A). A solution of 100 μl of A, 10 μl of EBT as color indicator and 10 ml of ammonia buffer was titrated with a solution of 5 mM CaCl₂ In this example, the result was around 0.855 μcool/mg.

Example 2: Synthesis of Ultrasmall Hybrid Chelating Silica Nanoparticles (UCHSNP) in Water Using Macrocyclic-Chelator-Functionalized Silane (APTES-DOTAGA) and Amino Silane (APTES)

In this example, the synthesis is divided into two steps. First, the silane precursor APTES-DOTAGA, which is not commercially produced yet, is synthesized. Then, the ultrasmall hybrid chelating silica nanoparticles (UCHSNP) functionalized with macrocyclic chelating agent DOTAGA are synthesized according to the method presented in example 1.

Step 1: Synthesis of the Macrocyclic-Chelator-Functionalized Silane (APTES-DOTAGA)

APTES-DOTAGA can be synthesized from 2 different methods: through the reaction between APTES and the activated carboxyl group on butyl protected DOTAGA by HBTU (2-(1H-benzotriazol-1-yl)-1,1,3,3-tetramethyluronium hexafluorophosphate), step 1a, or DOTAGA anhydride, step 1 b.

Figure 6:
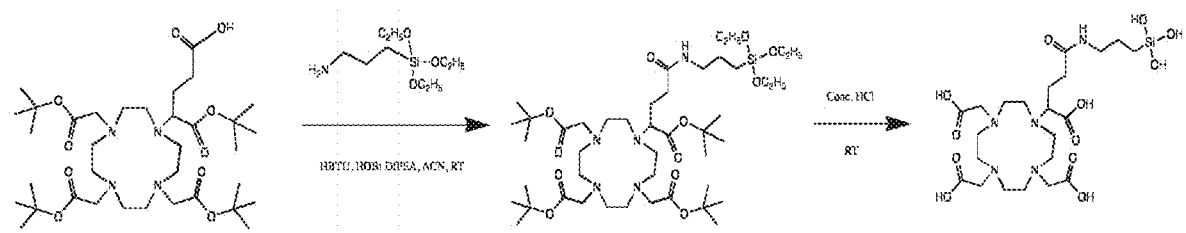

Step 1a: Synthesis of the Macrocyclic-Chelator-Functionalized Silane (APTES-DOTAGA) from Butyl Protected DOTAGA APTES-DOTAGA can be synthesized from the t-butyl protected DOTAGA which was coupled to APTES through peptide coupling. This was followed by the deprotection of the intermediate to get the final compound. The reaction scheme is presented in FIG. 6.

1 g of (t-Bu)$_4$DOTAGA, 0.6 g of HBTU and 0.2 g of HOBt were weighed into 100 ml round bottom flask to which 28 mL of DCM (dichloromethane) was added, followed by the addition of 1.3 ml of DIPEA. The mixture was stirred for 15 min, after which 0.3 g of APTES was injected into the reaction mixture. The solution was left for stirring overnight at room temperature.

The reaction mixture was diluted thrice to 90 ml using DCM followed by extraction of the reaction solution with 80-90 ml of citric acid solution (pH 3) in a separating funnel. The separated organic phase was further extracted with 80-90 ml of 5% w/v NaHCO$_3$ followed lastly by distilled water. Above extractions enabled to remove the coupling reagents/unreacted APTES/extraneous water soluble components. The isolated organic phase was dried over MgSO$_4$ (5 g) for 5 min and successively filtered to get a clear filtrate. The filtrate was evaporated using ROTAVAPOR at 30° C. to get the light brownish viscous residue (intermediate). The intermediate formation was verified using HRMS. m/z for C$_{44}$H$_{85}$N$_5$O$_{12}$Si: Calculated: 926.5856, Obtained: 926.5849 (M+Na)$^+$.

$^1$H NMR (500 MHz, CDCl$_3$) δ 0.4-0.7 (m, 2H), 0.7-0.8 (m, 1H), 1.0 (dd, J=9.0, 6.7 Hz, 1H), 1.1-1.2 (m, 9H), 1.3-1.5 (m, 32H), 1.5 (p, J=7.8 Hz, 2H), 1.7 (d, 1H), 1.9-2.1 (m, 1H), 2.1-2.3 (m, 1H), 2.4-3.4 (m, 29H), 3.5-3.7 (m, 1H), 3.7 3.8 (m, 4H).

$^{13}$C NMR (126 MHz, CDCl$_3$) δ 7.5, 7.8, 18.3, 20.4, 23.5, 25.9, 26.8, 27.8, 27.8, 27.9, 27.9, 27.9, 28.2, 28.3, 29.7, 33.0, 38.6, 42.1, 47.6, 49.8, 58.4, 63.6, 80.8, 82.3, 171.1, 173.2.

The above residue was mixed with 20 ml of concentrated HCl and stirred for 40 min followed by the removal of excess acid using rotary evaporator at 35° C. to get a solid residue. The residue was further dissolved in about 10 ml of water and subjected to rotary evaporation to remove free acid. The obtained concentrate was dissolved in 10 ml water and frozen immediately in nitrogen and lyophilized to get a light brown powder 1.11 g. m/z for C$_{22}$H$_{41}$N$_5$O$_{12}$Si: Calculated: 618.2413, Obtained: 618.2425 (M+Na)$^+$.

1H NMR (500 MHz, Deuterium Oxide) δ 0.5-0.8 (m, 2H), 1.2-1.3 (m, 1H), 1.4-1.6 (m, 1H), 1.6-1.8 (m, 1H), 1.8-2.2 (m, 1H), 2.3-4.5 (m, 26H).

Figure 7:
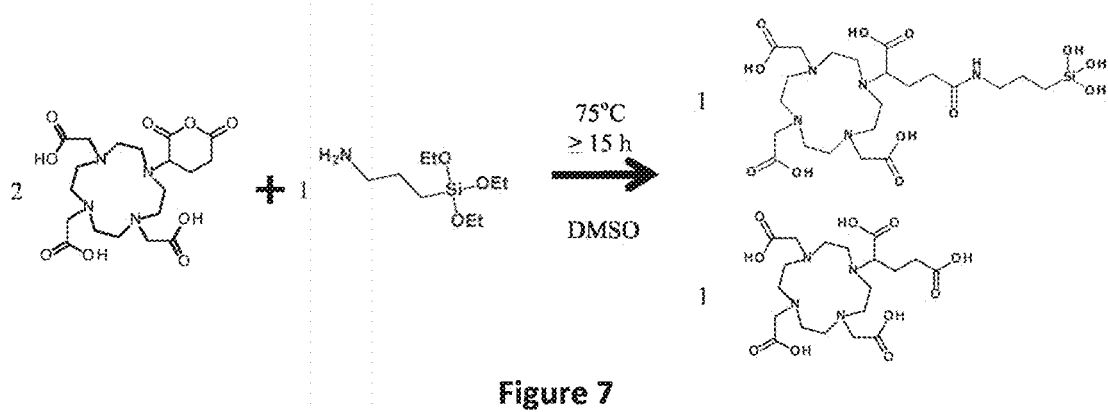
FIG. 7 shows the reaction scheme of the synthesis of APTES-DOTAGA according to example 2, step 1.b.

Step 1b: Synthesis of the Macrocyclic-Chelator-Functionalized Silane (APTES-DOTAGA) from DOTAGA Anhydride The silane precursor APTES-DOTAGA can also be synthesized from DOTAGA anhydride. The reaction scheme is presented in FIG. 7.

In a typical example, 9.375 g (16.36 mmol) of DOTAGA anhydride was put in a 1 L round flask. Then, 494 mL of anhydrous DMSO and 1.933 ml (8.16 mmol) of APTES were added quickly. DOTAGA anhydride was used in excess to make sure all APTES will react. This allows the precise control of the composition of the final particles in the next step. The reaction was put under argon atmosphere and heated to 75° C. during 15-20 h. The product formed as white precipitate. The product was fully precipitated by transferring it to 5 L of acetone and kept at 4° C. for 48 h. The precipitate was filtered through filter paper grade 42. Around 2-3 L acetone were used to wash the precipitate to remove DMSO. The remaining acetone was removed by evaporating at 37° C. overnight.

After the purification, the precipitate was dissolved in water and analyzed by HPLC according to method 2. By superimposing the chromatograms of the synthesis mixture with the ones of GdCl$_3$ and the mixture of GdCl$_3$ and DOTAGA(Gd$^{3+}$), the peaks can be identified). MS analysis was also performed in order to confirm the structure of the reaction product. The MS spectrum showed 4 main peaks at 594, 475, 296.5 and 237 m/z, which is in agreement with simulated spectra of the proposed products and indicates the co-presence of singly charged ions and doubly charged ions.

The content (mol/g) of APTES-DOTAGA in the synthesis mixture was determined indirectly through the content of total APTES-DOTAGA and unreacted DOTAGA determined by colorimetry and phosphorescence titration by Eu and the content of unreacted DOTAGA according to method 3 of chromatography.

For colorimetry, 200 μl of synthesis mixture at 8.815 mg/L and 25 μL of EBT (NET) was added to 10 mL of ammonia buffer pH 10. This solution was titrated with CaCl$_2$ 5 mM. The endpoint volume was 600 μl which gave the content of total DOTAGA as 1.70 μmol/mg. By using this result, a series of samples of synthesis mixture at 44.075 mg/L and increasing concentration of Eu$^{3+}$ (0 μM-140 μM) was prepared in acetate buffer pH 5 to more precisely determine the content of total DOTAGA. These samples were incubated at 80° C. for 48 h before the phosphorescence measurement. FIG. 8-A shows the emission spectrum of DOTAGA(Eu$^{3+}$) at 40 μM. Two emission peaks at 594 nm and 616 nm were found. —FIG. 8-B shows the titration curve at 594 nm (circles) and 616 nm (squares) respectively. The content of total DOTAGA was determined as 1.475 μmol/mg. This result is more precise since colorimetry tends to overestimate the result due to the difficulty of recognizing the point when the color started to change.

Using HPLC analysis and a calibration curve, the concentration of DOTAGA(Gd$^{3+}$) was calculated. The content of unreacted DOTAGA was deduced from this result. The calculated content of unreacted DOTAGA was 0.745 μmol/mg.

From the above results, the content of the expected product APTES-DOTAGA can be inferred to be 0.730 μmol/mg. This suggests nearly all APTES has reacted with the excess of DOTAGA to form APTES-DOTAGA and no APTES remains in the mixture. Calculation shows that the yield of the reaction was 99% and the isolated yield of the whole process i.e. reaction and filtration was 79%.

Infrared (IR) spectroscopy was also used to characterize APTES-DOTAGA. DOTAGA and the reaction mixture of APTES-DOTAGA were dissolved in water and adjusted to pH 2 to protonate carboxylic groups. This makes the peak at 1677 cm$^{-1}$ of C=O amide distinguishable from the one at 1713 cm$^{-1}$ of C=O carboxyl. The 2 solutions were dried at 80° C. for 4 days. IR spectra were acquired with dry powder.

Figure 8A:
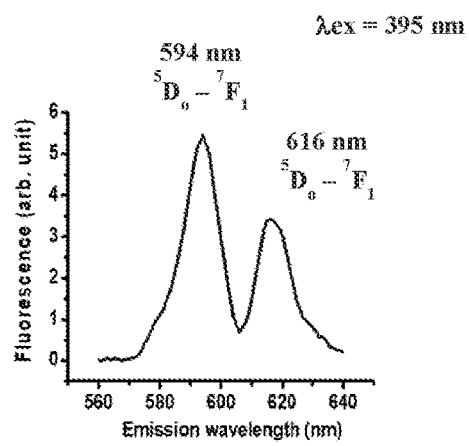
FIG. 8 shows the emission spectrum of a mixture of 40 μM $EuCl_3$ and 100 μM DOTAGA excited at 395 nm (FIG. 8A) and titration curve of APTES-DOTAGA synthesis mixture at 594 nm (circles) and 616 nm (squares) (FIG. 8B) according to example 2, step 1.b.
FIG. 8C shows the IR spectrum of DOTAGA according to example 2, step 1b.
FIG. 8D shows the IR spectrum of the reaction mixture of APTES-DOTAGA according to example 2, step 1b.
Figure 8B:
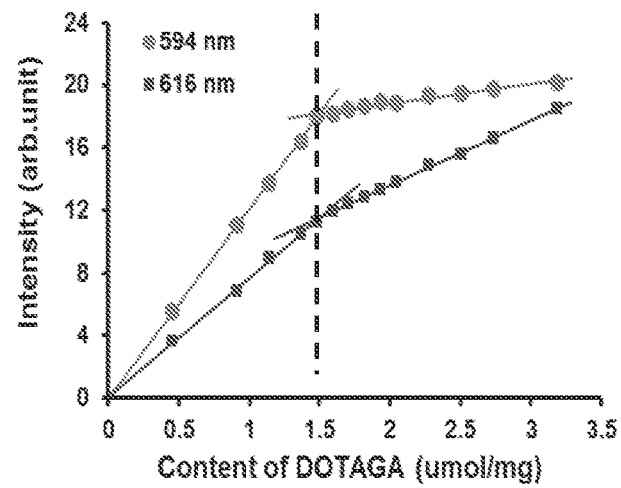
Figure 8C:
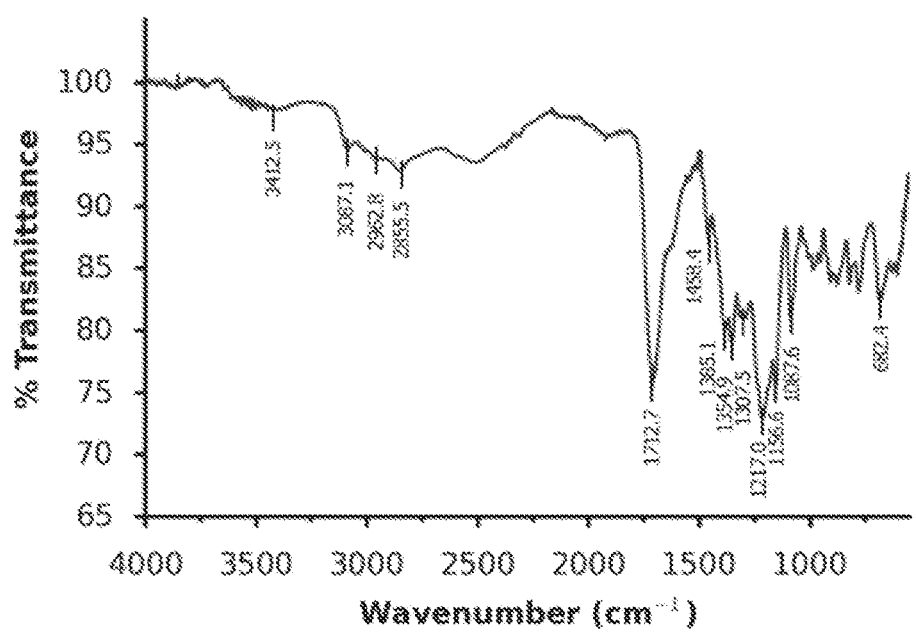
Figure 8D:
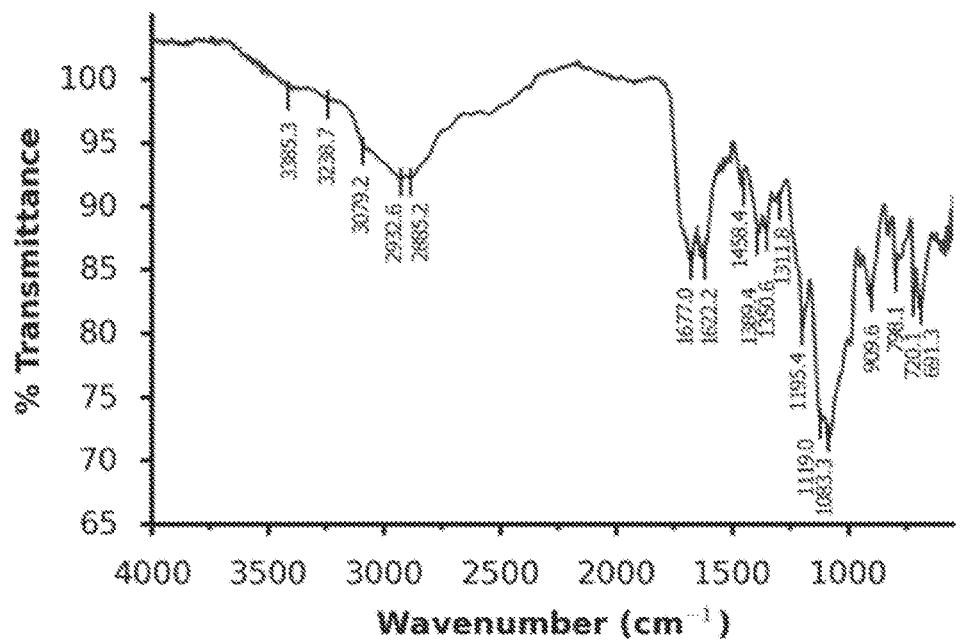

FIG. 8C shows the IR spectrum of DOTAGA powder and APTES-DOTAGA reaction mixture. The assignment for some important peaks is shown in Table 2 below. The appearance of peak at 1677.0 cm$^{-1}$, and the decrease of peak intensity at 1712.7 cm$^{-1}$ is an indication of the formation of the amide bond.

TABLE 2

Assignment of the main peaks in infra-red spectra of DOTAGA and APTES-DOTAGA

| Wave number (cm$^{-1}$) | Assignment |
|---|---|
| 3385.3 | Si—OH stretching or primary amine N—H stretching |
| 3238.7 | Si—OH stretching or secondary amide N—H stretching or carboxylic O—H stretching |
| 3079.2 | Secondary amide II overtone or carboxylic O—H stretching |
| 2932.6 | Methylene asymmetric C—H stretching |
| 2885.2 | Methylene symmetric C—H stretching |
| 1712.7 | Carboxylic acid C=O stretching |
| 1677.0 | Secondary amide C=O stretching |
| 1622.2 | Amine NH$_2$ scissoring, N—H bending |
| 1385.1 | Carboxylic acid C—O—H in-plane bending |
| 1221.3 | Carboxylic acid C—O stretching or Aliphatic C—N stretching |
| 1122.1 | Si—O—Si asymmetric stretching or Aliphatic C—N stretching |
| 1087.6 | Si—O—C stretching |

Step 2: Synthesis of the UCHSNP from APTES-DOTAGA

Two strategies can be employed to synthesize UCHSNP from APTES-DOTAGA:

a) APTES-DOTAGA silane can be used directly from the beginning to synthesize particles with free chelating agents on the surface (UCHSNP), then these UCHSNP will be complexed with Gd$^{3+}$ to form final products (UCHSNP@Gd-1); or b) APTES-DOTAGA silane can be complexed with Gd$^3$ before the hydrolysis-condensation process to create final particles with complexed chelates (UCHSNP@Gd-2).

Figure 9:
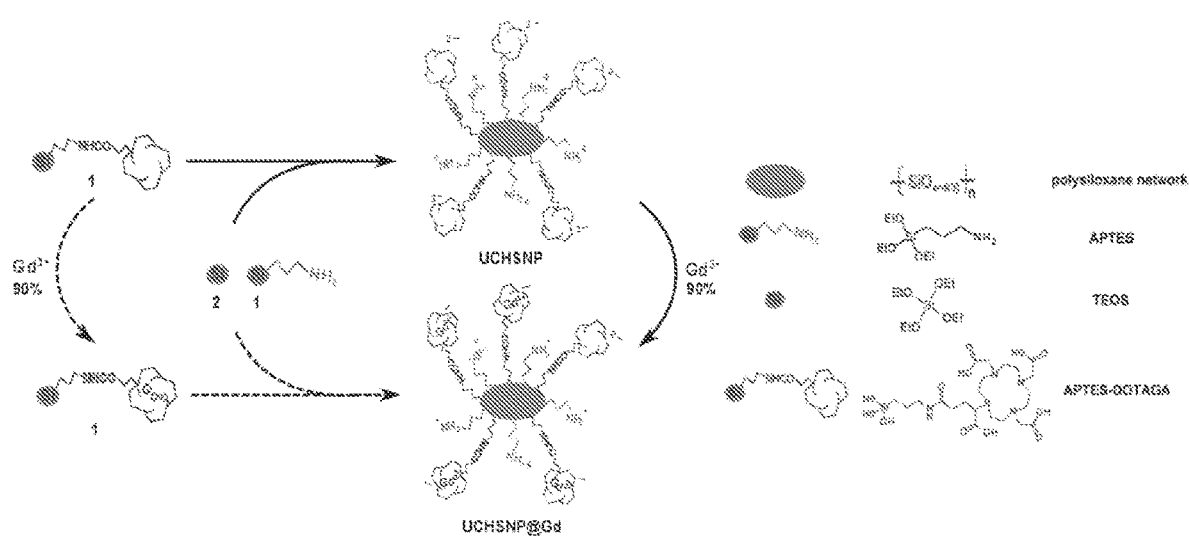
FIG. 9 shows the reaction scheme of the bottom-up synthesis of nanoparticles: strategy a (solid arrows) and strategy b (dashed arrows) according to example 2, step 2.

Both strategies are summarized in FIG. 9.

Step 2a Synthesis of the UCHSNP@Gd-1 from Empty APTES-DOTAGA 200 ml of water were added to the product synthesized from step 1a or 1b that, in either case, contains 2.228 mmol of APTES-DOTAGA. The pH of the solution was adjusted from around 3 to 9 by adding NaOH solutions with appropriate concentrations. The solution was stirred for 1-2 h to dissolve and liberate APTES-DOTAGA to monomer form. Then TEOS (1015.4 μL, 4.457 mmol) and APTES (526.7 μL, 2.228 mmol) were added one by one to the above solution. pH should be brought back to 9 if necessary since the addition of APTES slightly increases the pH. Water was added to achieve the final concentration of APTES-DOTAGA, TEOS and APTES at 10 mM, 20 mM and 10 mM respectively. The reaction mixture was stirred at 25° C. over night to let the solution become homogeneous which implies that all ethoxysilanes were hydrolyzed. Then, the pH was decreased from 9 to 7 by adding few drops of HCl at appropriate concentrations. The solution was left stirring for 2 h at 25° C. before being re adjusted from pH 7 to pH 4.5. The solution was stirred during 1-2 h more at 25° C. before being heated at 80° C. and gently stirred in an oil bath overnight (15-20 h). A little solution (1 mL) was filtered through 0.2 μm membrane and analyzed by DLS and HPLC (according to method 1). For HPLC analysis, two types of samples were prepared. Firstly, the filtered solution was quickly diluted 2 times to have a theoretical concentration of 5 g/L right before being injected to HPLC system. The signals were followed at 295 nm, which is a typical absorption of AGuIX particles. Secondly, 200 μL of the filtered solution was mixed with 5 μL of CuSO$_4$ 506 mM, an excess amount compared to the theoretical concentration of chelating agents in the solution. This solution was incubated at 80° C. for 2 h. The pH after incubation was verified and maintained at 3.23, which is low enough to avoid Cu(OH)$_2$ formation. After that, the solution was quickly diluted to a theoretical concentration of 5 g/L right before being injected to HPLC system. The signals were followed at 700 nm, which is a specific absorption peak of copper and its DOTAGA complex.

The solution was concentrated to 10 mL by ultrafiltration through Vivaspin™ (MWCO=3 kDa). Again, the HPLC analysis was repeated. The 2 samples, without copper and copper complexed were diluted to a theoretical concentration of 5 g/L right before being injected to HPLC system to compare with the previous results.

Then the solution was purified further with ultrafiltration. If the precursor was a mixture with unreacted DOTAGA, the pH of the solution should be adjusted to 2 by adding HCl solutions before the purification. This step deprotonated DOTAGA and released them from being attached electrostatically to amino groups on the surface of the newly formed particles. The solution was centrifuged until half of the volume remains (purification rate 2$^1$=2). This step was repeated several times, by filling the tubes with hydrochloric acid (HCl) solution 10$^{-4}$ M (or HCl solution 10$^{-2}$ M in case the filtration was carried out at pH 2) and centrifuging again, until the purity calculated from HPLC chromatogram reaches ≥90% (normally, 2$^{10}$=1024 purification rate). Then, the solution was filtered through 0.2 μm membrane to remove the dust. Finally, the solution was freeze dried for long term storage. 706 mg of lyophilized powder was obtained.

Figure 10:
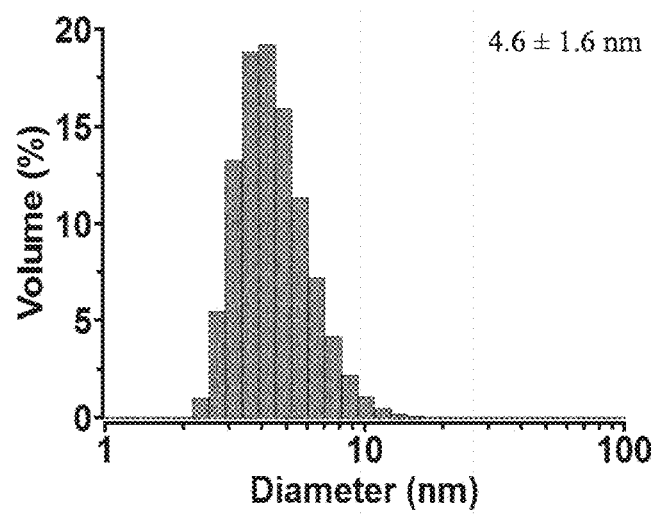
FIG. 10 shows the DLS diagram of the UCHSNP-1 nanoparticles according to example 2, step 2.a, before chelation with $Gd^{3+}$.

FIG. 10 shows the D$_H$ distribution of UCHSNP-1 that has formed. The particles have D$_H$ around 4.6±1.6 nm. HPLC analysis confirms that after the purification, the nanoparticles are pure and well grafted with DOTAGA on the surface. The latter was indicated by the chromatograms at 700 nm.

The content of DOTAGA in the final nanoparticles (UCHSNP-1) was quantified by two methods: 1) HPLC analysis with copper (using method 1) and 2) titration with Eu phosphorescence.

For the first method, a mixture containing 142.8 g/L of UCHSNP-1 and 200 mM of CuSO$_4$ was prepared at pH 3 and incubated at 80° C. for 2 h. Solution was diluted 20 times in HCl solution 10$^{-3}$ M immediately before being injected into the HPLC system. The HPLC chromatogram shows the presence of metal incorporated nanoparticles and free copper complexed APTES-DOTAGA. The R$_t$ of the metal incorporated nanoparticles is longer than the initial empty nanoparticles. This can be explained by the change of the surface charge or the ionization state induced by the complexation. More importantly, the shape of nanoparticles peak shows a homogenous distribution after the complexation. The total concentration of all copper species was 10.03 mM which is precisely equal to the amount theoretically introduced. From the results, we can find out the total concentration of DOTAGA in the sample and deduce its content which was about 0.72 μcool/mg.

Figure 11:
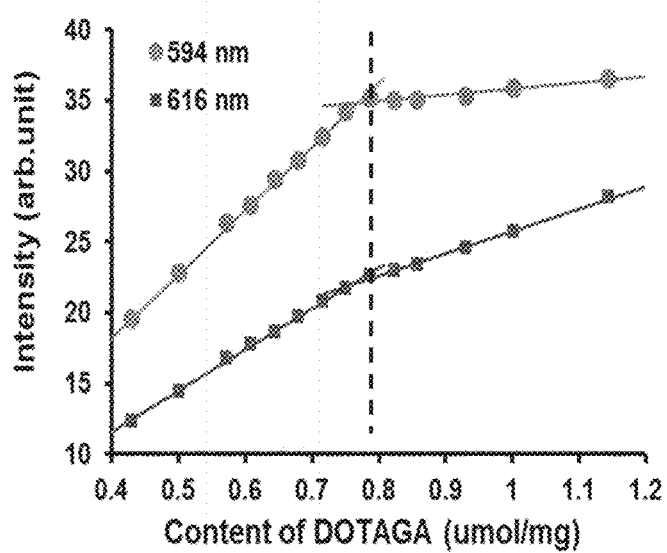

For the titration by Eu, a series of samples at 44.08 mg/L of UCHSNP-1 and 0 μM to 140 μM of EuCl$_3$ in acetate buffer pH 5 were prepared. These samples were incubated at 80° C. for 48 h before the measurement. FIG. 11 shows the titration curve at 2 specific emission wavelength of DOTA-GA(Eu$^{3+}$) complex. The result was 0.79 µmol/mg.

UCHSNP@Lu-1

To evaluate the diameter of UCHSNP-1, the presence and the ratio of APTES-DOTAGA and APTES on its surface, $^1$H NMR and NMR DOSY spectra were collected from empty UCHSNP-1 and UCHSNP-1 complexed with diamagnetic lanthanide ion i.e. Lu$^{3+}$ (UCHSNP@Lu-1).

For the empty UCHSNP-1 sample, the lyophilized powder was redispersed in water. The pH of the solution was adjusted to 7.4 before water was added to have a final concentration at 127 g/L or 100 mM in DOTAGA. The solution was lyophilized and redispersed in D$_2$O at the same concentration. Then, 470-500 µl of sample was added to the NMR tube for the measurement.

For the UCHSNP@Lu-1 sample, the lyophilized powder was redispersed in water. Using the content of DOTAGA calculated from Eu titration, 32.5 µL of LuCl$_3$ solution at 1.98 M (molar ratio DOTAGA:Lu=1:0.9) was added slowly in 4 times. Between each time, pH was carefully increased to 4-5 by adding NaOH solution with appropriate concentrations before adding the next one. After 4 additions, pH was at 5. This solution was incubated at 80° C. for 48 h. Finally, pH was increased to 7.4 and water was added to have a final concentration at 127 g/L or 100 mM in DOTAGA. The solution was lyophilized and redispersed in D$_2$O at the same concentration. Then, 470-500 µl of sample was added to the NMR tube for the measurement.

Figure 12:
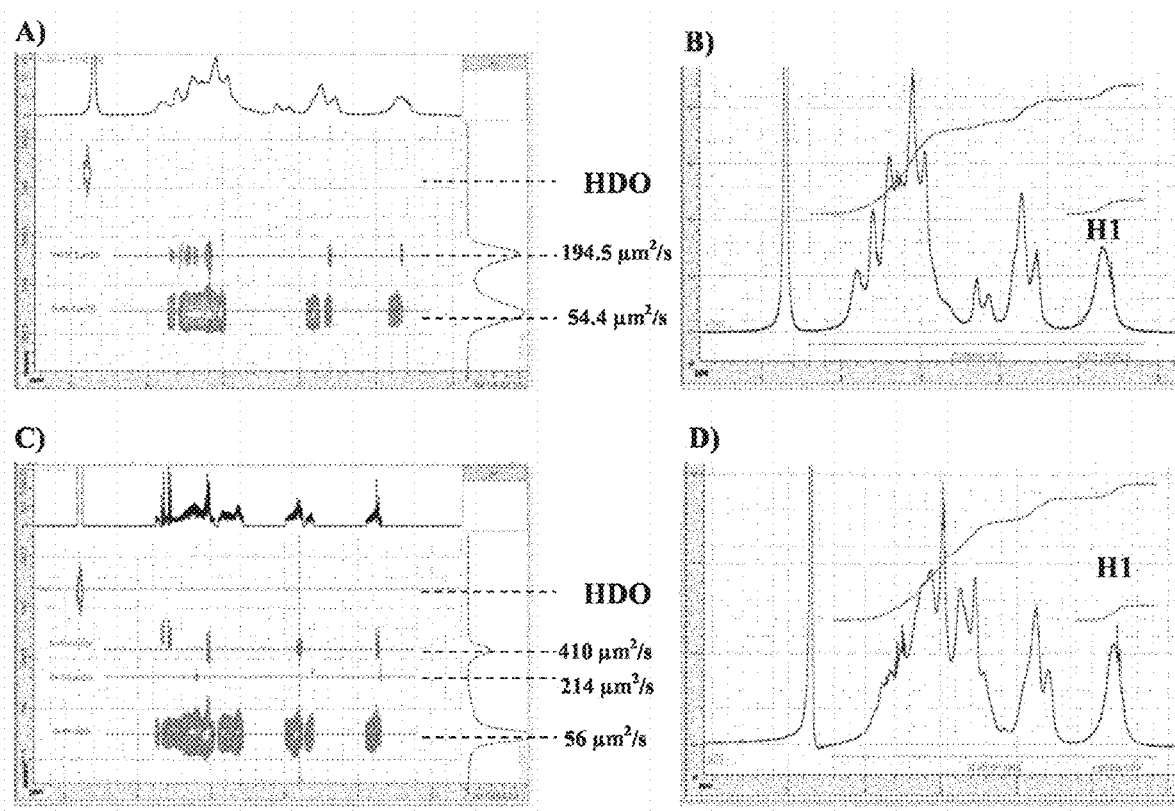

FIG. 12 shows NMR spectra of the UCHSNP-1. First of all, FIG. 12-A shows a 2D NMR ROSY spectrum in D$_2$O. Most of protons seem to have the same diffusion coefficient (D) at 54.4 µm$^2$/s. The result indicates that expected functional groups i.e. APTES-DOTAGA and APTES were well grafted on the same particles. Second, there are some free hydrolyzed silanes which have much faster coefficient (194.5 µm$^2$/s). Similar spectrum was found with UCHSNP-1@Lu (FIG. 12-C). The main products still had D around 56 µm$^2$/s. They coexisted with some other smaller species which have faster D (410 and 214 µm$^2$/s). Hydrodynamic diameter of the main particles can be calculated from Einstein equation which is around 7.0 nm and 6.8 nm for UCHSNP-1 and UCHSNP-1@Lu respectively. The viscosity of the solution was unknown and might be considerably higher than pure D$_2$O at this concentration. Therefore, the calculated D$_H$ might be a bit overestimated. In any case, it stayed less than 10 nm and was in accordance with the result measured from DLS. FIGS. 12-B and D shows the peak integration of 1D $^1$H spectrum of the UCHSNP-1 and UCHSNP-1@Lu. Most of $^1$H peaks were superimposed on each other due to the complex $^1$H spectrum of DOTAGA that could be confirmed elsewhere. Fortunately, DOTAGA has no $^1$H peak at the region smaller than 1 ppm where the peak of $^1$H of carbon at position 1, closest to Si of APTES and APTES-DOTAGA, can be found (FIG. 12-E). Therefore, by comparing the areas of $^1$H peaks coming from those carbons 1 with the total area of all $^1$H peaks, we can find out the ratio between the amount of APTES over the amount of APTES-DOTAGA in the sample. In these two samples, the result was 1.35 and 1.12 respectively.

UCHSNP@Gd-1

To enable UCHSNP-1 to have MRI contrast enhancing and radio sensitization properties, Gd$^{3+}$ was complexed on the particles. In a typical example, 333 mg of lyophilized powder of UCHSNP-1 was redispersed in water. 36 µL of GdCl$_3$ solution at 2.188 M (molar ratio DOTAGA:Gd=1:0.9) was added slowly in 3 times. Between each time, pH was carefully increased to 4-5 by adding NaOH solution with appropriate concentrations before adding the next one. After 3 additions, pH was at 5. This solution was incubated at 80° C. for 48 h. After the incubation, pH was maintained. This solution was purified by tangential filtration (MWCO=3 kDa) with 5 purification rates to get rid of any free Gd$^{3+}$. The purity of the solution was evaluated by HPLC (method 1). The purified solution (~1 ml) was diluted 52 times with HCl 10$^{-2}$ M solution to have a theoretical concentration of 5 mM in DOTAGA right before being injected into HPLC system.

The R$_t$ of the Gd$^{3+}$ incorporated nanoparticles is longer than the Cu$^{2+}$ incorporated nanoparticles and the initial empty nanoparticles. This can be again explained by the change of the surface charge or the ionization state induced by the complexation because the DOTAGA(Gd$^{3+}$) has all four carboxylate groups in coordination with the metal whereas the DOTAGA(Cu$^{2+}$) has two free carboxylate groups. More importantly, as in the case of copper incorporated nanoparticles, the shape of the nanoparticles peak shows a homogenous distribution after the complexation.

The HPLC chromatogram shows that the nanoparticles are pure. The purity of the solution was evaluated from the chromatogram at 295 nm and was nearly 100%.

Next, pH of the solution was increased to 7.4 and the solution was filtered through 0.2 µm membrane to remove the dust before being lyophilized. In this example, 250 mg of powder of UCHSNP@Gd-1 was obtained.

Figure 13:
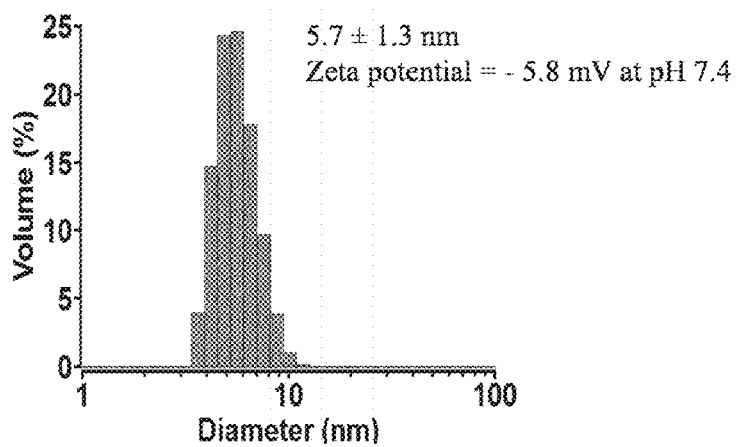
FIG. 13 shows the DLS diagram and zeta potential of UCHSNP@Gd-1 according to example 2, step 2.a, redispersed from lyophilized powder after chelation with $Gd^{3+}$.

A sample of lyophilized powder was redispersed in water to verify the hydrodynamic diameter (D$_H$), surface charge and the relaxivity (r$_1$ and r$_2$). FIG. 13 shows the distribution histogram of D$_H$ of UCHSNP@Gd-1 that was 5.7±1.3 nm. The surface charge was reflected by the zeta potential value which was −5.8 mV at pH 6.65 and −8.2 mV at pH 7.34. Then, elemental analysis was performed to reveal the chemical composition of the particle. From this result, the content of Gd was 0.60 µmol/mg (Table 3). Next, the relaxation times (T$_1$ and T$_2$) of a solution of UCHSNP@Gd-1 in water at 100 g/l (60.4 mM in Gd) were measured to give r$_1$=21.4 (s$^{-1}$·mM$^{-1}$) and r$_2$=34.1 (s$^{-1}$·mM$^{-1}$) at 37° C. and under 1.4 T.

Step 2b: Synthesis of the UCHSNP@Gd-2 from Complexed APTES-DOTAGA(Gd$^{3+}$)

200 ml of water were added to 2.333 mmol of APTES-DOTAGA synthesized from step 1a or 1b. The pH of the solution was adjusted to 4 by adding NaOH solutions with appropriate concentrations. 1.938 mL of GdCl$_3$ solution at 2.188 M (molar ratio (APTES-DOTAGA+DOTAGA): Gd=1:0.9) was added in 3 times. Between each time, pH was carefully increased to 4-5 by adding NaOH solution with appropriate concentrations before adding the next one. After 3 additions, pH was at 5. This solution was incubated at 80° C. pH was verified and re-adjusted to 5 after each 24 h. After 48 h of incubation, pH maintained at 5 steadily.

Then the pH of this solution was adjusted to 9 and the solution was stirred for 1-2 h to dissolve and liberate APTES-DOTAGA(Gd$^{3+}$) to monomer form. Then TEOS (1015.4 µL, 4.457 mmol) and APTES (526.7 µL, 2.228 mmol) were added one by one to the above solution. pH should be brought back to 9 if necessary since the addition of APTES slightly increases the pH. Water was added to achieve the final theoretical concentration of APTES-DOTAGA(Gd$^{3+}$), APTES-DOTAGA, TEOS and APTES at 9 mM, 20 mM and 10 mM respectively. The reaction mixture was stirred at 25° C. over night to let the solution become homogeneous which implies that all ethoxysilanes were hydrolyzed. Then, the pH was decreased from 9 to 7 by adding few drops of HCl at appropriate concentrations. The solution was left stirring for 2 h at 25° C. before being re adjusted from pH 7 to pH 4.5. The solution was stirred during 1-2 h more at 25° C. before being heated at 80° C. and gently stirred in an oil bath overnight (15-20 h). A little solution was filtered through 0.2 μm membrane and analyzed by DLS and HPLC (according to method 1). For HPLC analysis, the filtered solution was quickly diluted 2 times to have a theoretical concentration of 5 g/L right before being injected to HPLC system. The signals were followed at 295 nm. In addition, fluorescence detector ($\lambda_{ex}$=274 nm, $\lambda_{em}$=312 nm) was also used to qualitatively detect the presence of Gd complexes.

Then the solution was concentrated to 10 ml by Vivaspin™ (MWCO=3 kDa). Again, the HPLC analysis was repeated. Sample was diluted to theoretical concentration 5 g/L right before being injected to HPLC system to compare with the previous result.

Then the solution was purified further with ultrafiltration. If the precursor was a mixture with unreacted DOTAGA, the pH of the solution should be adjusted to 2 by adding HCl solutions before the purification. The purification was carried out until the purity calculated from HPLC chromatogram reaches ≥90% (10 purification rates). Then, pH of the solution was increased to 7.4 before being lyophilized. It was filtered through 0.2 μm membrane to remove the dust and large particles before being freeze-dried for long term storage. In this example, 716 mg of powder of UCHSNP@Gd-2 was obtained.

Figure 14:
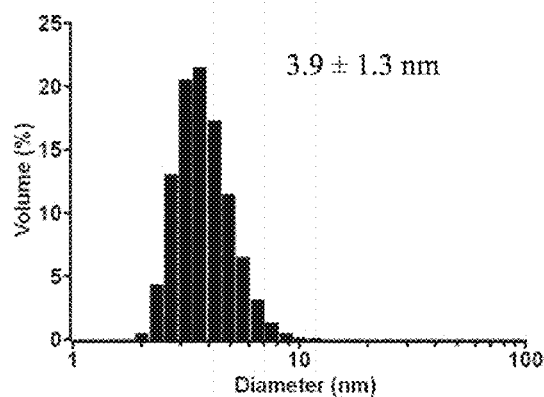
FIG. 14 shows the DLS diagram of UCHSNP@Gd-2 nanoparticles before concentrated according to example 2, step 2.b.

FIG. 14 shows the $D_H$ distribution of UCHSNP@Gd-2 that has formed. The particles have $D_H$ around 3.9±1.3 nm.

The HPLC chromatogram shows that after the purification, the nanoparticles are pure and well grafted with DOTAGA on the surface. The shape of the peak shows a homogenous distribution after the complexation. The purity of the solution was evaluated from the chromatogram at 295 nm and was 96.8%.

Figure 15:
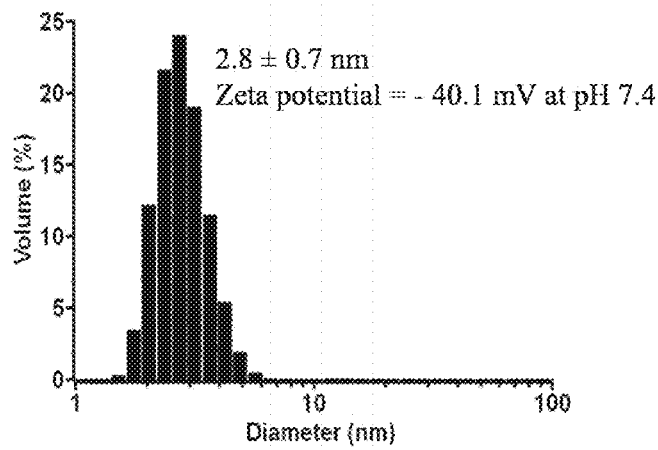
FIG. 15 shows the DLS diagram and zeta potential of UCHSNP@Gd-2 nanoparticles redispersed from lyophilized powder after purification according to example 2, step 2.b.

A sample of lyophilized powder was redispersed in water to verify the $D_H$, surface charge and the relaxivity ($r_1$ and $r_2$) after lyophilization. FIG. 15 shows the distribution histogram of $D_H$ of UCHSNP@Gd-2 that was 2.8±0.7 nm. The surface charge was reflected by the zeta potential value which was −35.6 mV at pH 7.4. Then, elemental analysis was also performed to reveal the chemical composition of the particle. From this result, the content of Gd was 0.63 μmol/mg (Table 3). According to the ratio of composition inferred from this result, UCHSNP@Gd-2 has less APTES and more free DOTAGA in its structure which explain a more negative zeta potential measured with these nanoparticles.

Figure 16:
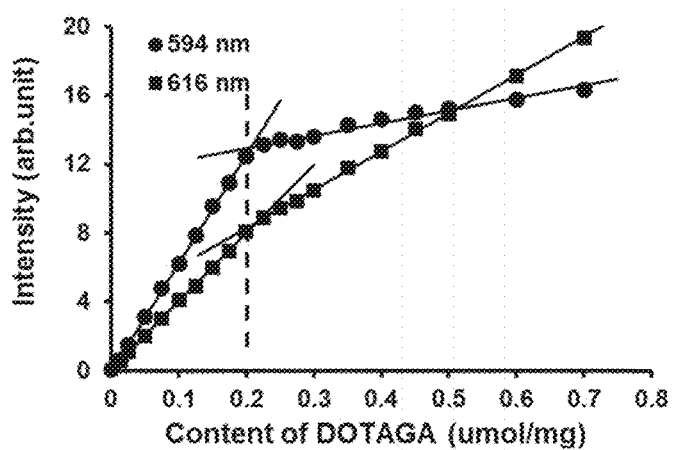
FIG. 16 shows the titration curve of UCHSNP@Gd-2 sample at 594 nm (circles) and 616 nm (squares) excited at 395 nm according to example 2, step 2.b.

The content of free DOTAGA on UCHSNP@Gd-2 was verified by another titration with Eu (FIG. 16). The result showed that effectively at least 0.20 μmol/mg of DOTAGA or 24.1% can react with metals among total content of 0.94 μmol/mg of DOTAGA. This is higher than in the case of UCHSNP@Gd-1 (10%). The contents of total APTES-DOTAGA suggested by elemental analysis are always 10% higher than the values estimated by the titration indicating some DOTAGA in both nanoparticles are not accessible to the metals.

The higher amount of free DOTAGA in UCHSNP@Gd-2 might be attributed to the decomplexation which was accelerated when the reaction mixture was stirred at pH 9 overnight to hydrolyze TEOS. The lower amount of APTES in UCHSNP@Gd-2 compared to UCHSNP@Gd-1 can be explained by the difference in the charge of APTES-DOTAGA and APTES-DOTAGA($Gd^{3+}$). At pH 4.5, free form of DOTAGA is 2 or −3 when the complexed form is always at −1. Probably, the complexed form has a weaker charge repulsion that makes them more ready than the free form to compete with aminosilanes to have a position on the polysiloxane surface created by TEOS.

Next, the relaxation times ($T_1$ and $T_2$) of a solution of UCHSNP@Gd-2 in water at 100 g/l (63.0 mM in Gd) were measured to give $r_1$=18.5 ($s^{-1} \cdot mM^{-1}$) and $r_2$=28.7 ($s^{-1} \cdot mM^{-1}$) at 37° C. and under 1.4 T.

Table 4 summarizes the characteristics and properties of UCHSNP, UCHSNP@Gd-1 and UCHSNP@Gd-2.

TABLE 3

Elemental analysis of nanoparticles

| Batch | UCHSNP | Ratio | Content (μmol/mg) | UCHSNP@Gd-1 | Content (μmol/mg) | UCHSNP@Gd-2 | Content (μmol/mg) |
|---|---|---|---|---|---|---|---|
| % mass Gd | 0.0000 | | | 9.5000 | | 9.9000 | |
| relative mol Gd | 0.0000 | | | 1.0000 | | 1.0000 | |
| % mass Si | 19.0000 | | | 18.0000 | | 17.0000 | |
| relative mol Si | 1.1845 | | | 10.6069 | | 9.6129 | |
| % mass C | 28.6000 | | | 24.1000 | | 25.9000 | |
| relative mol C | 4.1703 | | | 33.2155 | | 34.2541 | |
| % mass N | 8.0000 | | | 6.8000 | | 7.0000 | |
| relative mol N | 1.0000 | | | 8.0341 | | 7.9363 | |
| relative mol Gd | 0.0000 | | 0.0000 | 1.0000 | 0.6041 | 1.0000 | 0.6296 |
| relative mol APTES-DOTAGA | 0.1672 | 1.0000 | 0.9547 | 1.3019 | 0.7865 | 1.4922 | 0.9394 |
| relative mol APTES | 0.1640 | 0.9812 | 0.9367 | 1.5247 | 0.9211 | 0.4753 | 0.2992 |
| relative mol TEOS | 0.8533 | 5.1038 | 4.8725 | 7.7803 | 4.7003 | 7.6454 | 4.8133 |
| free chelators | | | | | 0.1824 | | 0.3099 |
| % free chelators | | | | 23.1883 | | 32.9844 | |

TABLE 4

Characteristics and properties of UCHSNP, UCHSNP@Gd-1 and UCHSNP@Gd-2

| Properties | Method(s) | UCHSNP | UCHSNP@Gd-1 | UCHSNP@Gd-2 |
|---|---|---|---|---|
| Starting ratio A-D:A:T (:Gd)* | — | 1 A-D:1 A:2 T | 1 A-D:1 A:2 T:0.9 Gd | 1 A-D:1 A:2:0.9 Gd |

TABLE 4-continued

Characteristics and properties of UCHSNP, UCHSNP@Gd-1 and UCHSNP@Gd-2

| Properties | Method(s) | UCHSNP | UCHSNP@Gd-1 | UCHSNP@Gd-2 |
|---|---|---|---|---|
| Total silane concentration (mM) | — | 40 | — | 40 |
| $D_H$ (nm) | DLS | 4.6 ± 1.6 | 5.7 ± 1.3 | 2.8 ± 0.7 |
| $D_H$ (nm) | NMR DOSY | 7.0 ± 2.5 (empty) 6.8 ± 2.4 ($Lu^{3+}$) | — | — |
| Zeta potential (mV) | Zeta potentiometry | −21.4 (pH 6.63) −27.1 (pH 7.37) | −5.8 (pH 6.65) −8.2 (pH 7.34) | −35.6 (pH 7.38) |
| Purity (%) | HPLC (295 nm) | 97.6 | ~100 | 96.8 |
|  | HPLC ($Cu^{2+}$) | 93.9 | — | — |
| DOTAGA content (μmol/mg) | $Eu^{3+}$ titration | 0.787 | — | — |
|  | HPLC ($Cu^{2+}$) | 0.715 | — | — |
| $r_1$ ($mM^{-1} \cdot s^{-1}$) (37° C., 60 MHz) | Relaxometry | — | 21.4 | 18.5 |
| $r_2/r_1$ (37° C., 60 MHz) | Relaxometry | — | 1.59 | 1.55 |
| A/A-D | 1H NMR | 1.35 (empty) 0.87 ($Lu^{3+}$) | — | — |
| Gd content (μmol/mg) | ICP-OES | — | 0.604 | 0.630 |
| (Gd:) Si:N:C (% mass) | Elemental analysis | 19.0 Si:8.0 N:28.6 C | 9.5 Gd:18 Si:6.8 N:24.1 C | 9.9 Gd:17.0 Si:7.0 N:25.9 C |
| A-D:A:T (:Gd) (molar ratio) | Elemental analysis | 1.0 A-D:1.0 A:5.1 T | 1.0 A-D:1.2 A:6.0 T:0.8 Gd | 1.0 A-D:0.3 A:5.1 T:0.7 Gd |
| Free DOTAGA (%) | $Eu^{3+}$ titration | 100 | 10 | 24 |
| Free DOTAGA (%) | Elemental analysis | 100 | 23.2 | 33.0 |
| Yield (%) (in DOTAGA) | — | 9.2 | 6.9 | 10.7 |
| Yield (%) (in Gd) | — | — | 64 | 10.6 |

*A-D: APTES-DOTAGA, A: APTES, T: TEOS,

Example 3: Synthesis of UCHSNP with Different Sizes

Figure 17:
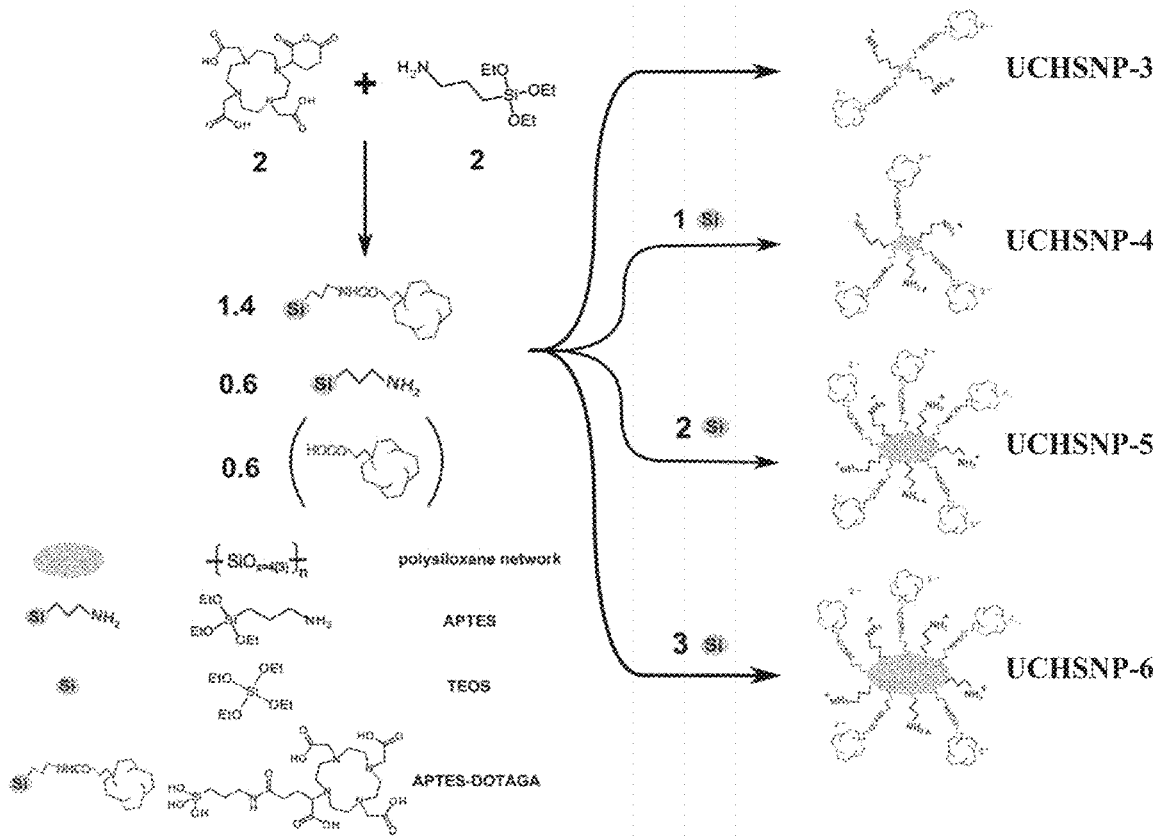
FIG. 17 shows the reaction scheme of the one-pot synthesis of nanoparticles and size controlling by adjusting the ratio of silanes according to example 3.

The synthesis can be further simplified by combining the synthesis of APTES-DOTAGA and the synthesis of polysiloxane particle into a one-pot protocol. Furthermore, the size of the particles can be controlled by changing the ratio of silane precursors in the formula (FIG. 17).

8 g of DOTAGA anhydride (13.96 mmoles) was put in a 100 mL round flask to which 31.6 mL of DMSO anhydrous and 3.300 mL of APTES (13.96 mmoles) was quickly added. The reaction was stirred under argon atmosphere and heated to 75° C. during 15-20 h. Unlike in the second example, the product is soluble due to the presence of excessive APTES which ionizes the carboxyl groups of DOTAGA. The mixture was let to cool down to room temperature before 663 mL of ultrapure water was added. The final percentage of DMSO in the solvent should be less than 5% not to dissolve the tangential filtration membrane used in the next step. A small amount of sample was taken to quantify the amount of produced APTES-DOTAGA by the combination of Eu titration and HPLC probed by $Gd^{3+}$ introduced before.

The pH of the solution was adjusted to 9 by adding NaOH solution and the mixture was stirred for 1 h to well liberate APTES-DOTAGA in monomer form. Then the solution was separated in 4 volumes. Increasing amounts of TEOS and water were added to each volume as shown in Table 5 to make sure the total silane concentrations in all samples are 20 mM. The pHs of the final solutions were verified and re-adjusted to 9 if necessary. These solutions were stirred at 25° C. overnight. Table 6 shows the ratios A, B and C between the different silanes used.

TABLE 5

The added amounts of TEOS, $H_2O$ and the composition of different formulas in example 2

| Formula code | TEOS (mmole) | $H_2O$ (ml) | APTES-DOTAGA:APTES:TEOS (mM) |
|---|---|---|---|
| UCHSNP-3 | 0 | 0.819 | 14.0:6.0:0.0 |
| UCHSNP-4 | 1.814 | 91 | 9.3:4.0:6.7 |
| UCHSNP-5 | 3.466 | 173 | 7.0:3.0:10.0 |
| UCHSNP-6 | 5.199 | 260 | 5.6:2.4:12 |

TABLE 6 ratios A, B and C

| Formula code | Ratio A | Ratio B | Ratio C |
|---|---|---|---|
| UCHSNP-3 | 0 | 0.43 | 0.42 |
| UCHSNP-4 | 0.72 | 0.43 | 1.1 |
| UCHSNP-5 | 1.42 | 0.43 | 1.85 |
| UCHSNP-6 | 2.14 | 0.43 | 2.57 |

Figure 18:
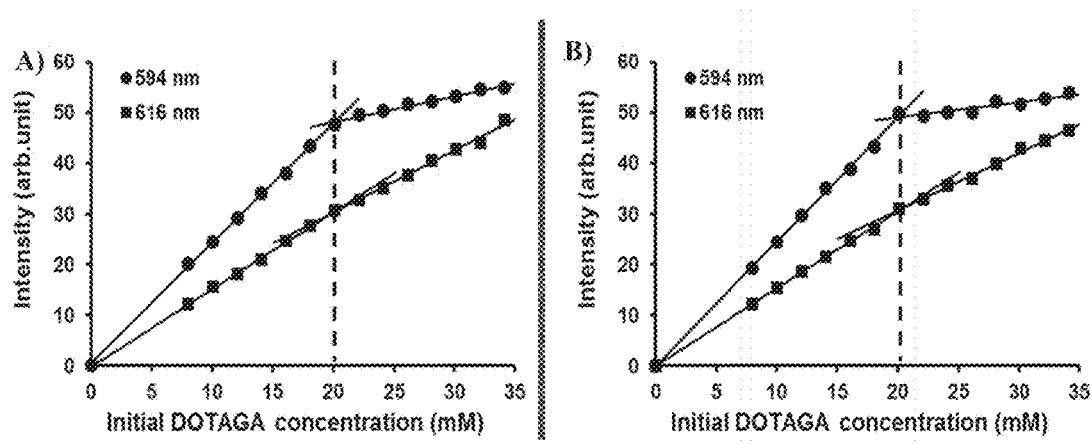
FIG. 18 shows the Eu titration curve of the mixture after the reaction between APTES and DOTAGA anhydride (FIG. 18A) and the same mixture exposed at pH 9 overnight (FIG. 18B) according to example 3.

With UCHSNP-3, the sample in which no TEOS was added, a small amount of sample was taken to verify the amount of APTES-DOTAGA after being exposed to basic pH overnight. FIG. 18 shows the result of Eu titration for 2 samples: before (A) and after (B) exposed to basic pH overnight. HPLC analysis was also performed. Table 7 summarizes the results of these tests.

TABLE 7

Summary of the result of the total DOTAGA and unreacted DOTAGA concentration

| Features | Method | | Result |
|---|---|---|---|
| [DOTAGA$_{total}$] (mM) | Titration with Eu$^{3+}$ | After the reaction In pH 9 overnight | 20 20 |
| [DOTAGA$_{unreacted}$] (mM) | HPLC (C18 column, Gd$^{3+}$) | After the reaction In pH 9 overnight | 6.21 (30.9%) 5.91 (29.4%) |

It is clear that the exposure to pH 9 affects neither the DOTAGA structure nor the amide bond of APTES-DOTAGA. Slight variation between DOTAGA peaks might be due to the difference in the room temperature. Finally, according to the result, around 70% of DOTAGA anhydride has reacted. With this, we can recalculate the precise amount of composition in 4 samples of nanoparticles as shown in Table 5.

Figure 19:
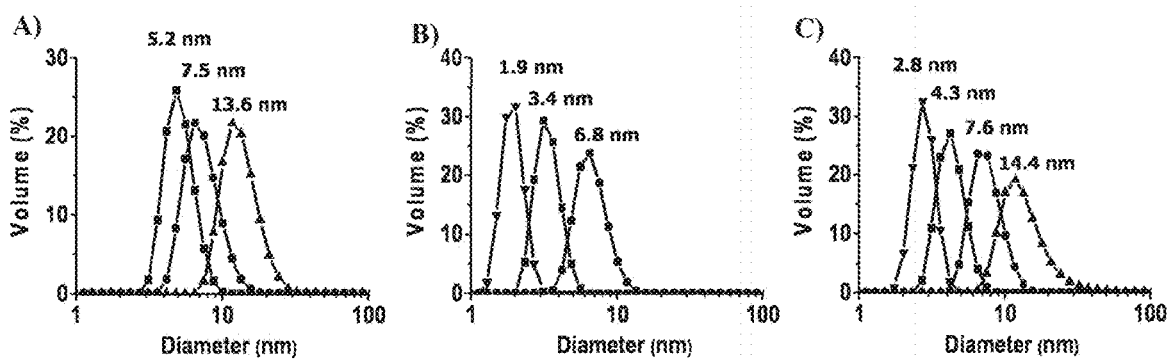
FIG. 19 shows the DLS diagram of nanoparticles with different ratio of starting silanes according to example 3.

The day after, pH of the 4 solutions were readjusted to 7. They were stirred for 1 h before their pHs were readjusted to 4.5. The solutions were stirred for another hour before they were heated to 40° C. overnight. 1 mL of these solutions was taken for DLS measurement (FIG. 19-A). The signal from UCHSNP-3 was too weak to have a reliable value which implies the creation of very small nanoparticles and/or a diluted concentration of nanoparticles. The other 3 samples showed a clear dependence of nanoparticle size on the added amount of TEOS. D$_H$ of UCHSNP-4, 5 and 6 are 5.2, 7.5 and 13.6 nm respectively.

These solutions were concentrated by Vivaspin (MWCO=3 kDa) to appropriate volumes in which the theoretical concentration of APTES-DOTAGA reaches 200 mM. Then the pH of the solutions was adjusted to 2 to release the unreacted DOTAGA and APTES-DOTAGA from their electrostatic interactions to the amines on the surface of newly formed nanoparticles. Solutions were purified at this pH by Vivaspin for 64 purification rates using HCl 10$^{-2}$ M as washing solvent. A small sample of each purified solution was diluted 40 times in HCl 10$^{-2}$ M right before being injected to HPLC for analysis with UV absorption at 295 nm. The more TEOS added in the formula, the slower the retention time of the nanoparticles. This indirectly shows the dependence of nanoparticles size to the amount of TEOS since a higher t$_R$ usually implies bigger nanoparticles. The data was summarized in Table 8.

TABLE 8

Summary of the chromatography result of nanoparticles with different ratio of starting silanes

| Formula code | APTES-DOTAGA:APTES:TEOS | Purity (%) | t$_R$ (min) | Peak area (arb. unit) | FWHM (min) |
|---|---|---|---|---|---|
| UCHSNP-3 | 14.0:6.0:0.0 | 94.0 | 12.4 | 833 | 1.1250 |
| UCHSNP-4 | 9.3:4.0:6.7 | 97.1 | 12.9 | 3231 | 0.9917 |
| UCHSNP-5 | 7.0:3.0:10.0 | 90.1 | 13.4 | 3794 | 0.8417 |
| UCHSNP-6 | 5.6:2.4:12 | 88.6 | 13.5 | 4128 | 0.4750 |

After the purification, the solutions were filtered through 0.2 μm membrane to remove the dust and other large particles before being freeze-dried for long term storage.

A small quantity of 4 samples was redispersed in water at 100 g/L. Since the pHs of the solutions were not adjusted before the lyophilization, after redispersed, their pHs stay around 2. Powder of UCHSNP-6 was not able to disperse again in water at this pH. These mother solutions were quickly diluted to 10 g/L with HCl 10$^{-2}$ M before being measured in DLS.

Another series of samples was redispersed at 150 g/L. NaOH solution was added to neutralize samples to pH 7. In this condition, it was possible to redisperse UCHSNP-6. Depending on the sample, water was added or not to obtain the final concentration around 80-100 g/L. Similarly, these mother solutions were quickly diluted to 10 g/L with water before being measured in DLS.

FIG. 19-B shows the hydrodynamic diameter distribution of 3 samples, UCHSNP-3,4,5, at pH 2. Meanwhile FIG. 19-C shows the results for 4 samples obtained at pH 7. Together, they show clearly the increase of NP size while TEOS was increased in the formula. The data are summarized in Table 9.

TABLE 9

Summary of the DLS results of NPs with different ratio of starting silanes

| Formula code | APTES-DOTAGA:APTES:TEOS | D$_H$ after synthesized (nm) | D$_H$ redispersed pH 2 (nm) | D$_H$ redispersed pH 7 (nm) |
|---|---|---|---|---|
| UCHSNP-3 | 14.0:6.0:0.0 | too weak signal | 1.9 ± 0.3 | 2.8 ± 0.5 |
| UCHSNP-4 | 9.3:4.0:6.7 | 5.2 ± 1.2 | 3.4 ± 0.6 | 4.3 ± 0.9 |
| UCHSNP-5 | 7.0:3.0:10.0 | 7.5 ± 2.1 | 6.8 ± 1.7 | 7.6 ± 1.9 |
| UCHSNP-6 | 5.6:2.4:12 | 13.6 ± 3.9 | precipitated | 14.4 ± 7.1 |

The fact that UCHSNP-6 could not be redispersed at pH 2 might be due to its lower colloidal stability explained by a bigger size, higher ratio of TEOS and lower density of protective layer of APTES-DOTAGA and APTES around it. It is worth to mention that, at this pH, 4 carboxyl groups of DOTAGA were protonated. Therefore, the repulsion between particles relies only on the positive charge of amino groups of APTES which is, however, quite short and the hindrance effect of DOTAGA. That explains why, at pH 7, UCHSNP-6 could be redispersed without problem. In this case, 2 carboxyl groups of DOTAGA were deprotonated and increase the total repulsion force. The results at pH 7 are very similar to the values before the purification (FIG. 19-A) implying that most particles remain intact during the procedure. The diameters at pH 7 were slightly bigger than the ones at pH 2. Probably, this is due to the repulsion between deprotonated DOTAGA on each particle that makes them more outspreaded. In short, this results show that by varying the ratio of siloxane network creator, TEOS, and organosilanes, APTES-DOTAGA and APTES, we can control the size of the NP. In this example, at ratio TEOS:(APTES-DOTAGA+APTES) 1:1, nanoparticle size exceeds 6 nm, the recommended limit for fast renal clearance. At ratio 1.5:1, its size would go beyond 10 nm, more specifically reach 14 nm.

Figure 20:
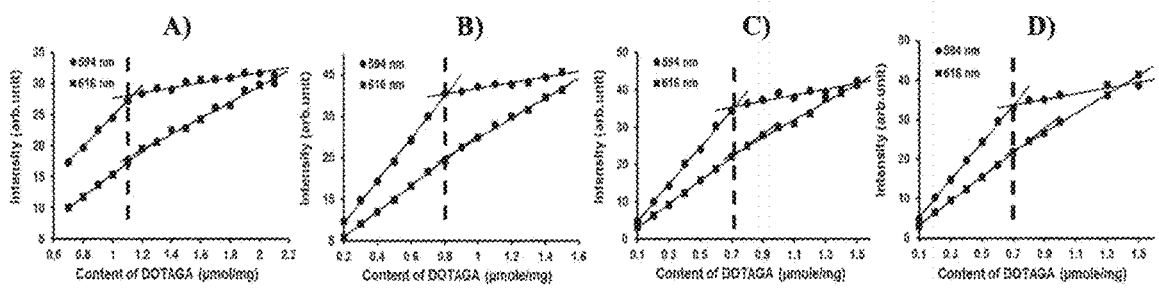
FIG. 20 shows the Eu titration curves of UCHSNP-3 (FIG. 20A), UCHSNP-4 (FIG. 20B), UCHSNP-5 (FIG. 20C) and UCHSNP-6 (FIG. 20D) according to example 3.

The DOTAGA content of each sample was determined by Eu titration as shown in FIG. 20. We see clearly a decrease of DOTAGA content when TEOS was increased in the formula as expected. Interestingly, the more TEOS we put, the higher of yield of APTES-DOTAGA at the end. Presumably, the siloxane bond between silicic acid and organosilanol is stronger than the siloxane bond between the organosilanols themselves. In addition, aminosilanes, especially the ones with short carbon chain such as APTES, are known as having quite low hydrolytic stability.

The nanoparticles UCHSNP-3, UCHSNP-4, UCHSNP-5 and UCHSNP-6 were also characterized by relaxometry and elemental analysis. Table 10 summarizes the properties and characteristics of UCHSNP-3, UCHSNP-4, UCHSNP-5 and UCHSNP-6.

Example 4: One not Medium Scale Synthesis of UCHSNP in Diethylene Glycol (UCHSNP-7) and its Complexation of Different Metals 6.187 ml of APTES (26.17 mmol) was added in a 200 ml glass bottle containing 90 ml of diethylene glycol (DEG). The solution was stirred at RT for 1 h before 10 g of DOTAGA anhydride (17.45 mmole) was added. The mixture was stirred at RT for 6 days to allow a complete reaction. The product was a fine suspension. A small amount of sample was taken and diluted 10 times in water to measure $D_H$ in DLS.

7.952 ml of TEOS (34.90 mmol) was added to the suspension. This mixture was stirred for 1 h. A small amount of sample was taken and diluted 10 times in water to measure $D_H$ in DLS. Then 900 ml of ultrapure water was added. The final percentage of DEG in the solvent should be less than 10% not to dissolve the tangential filtration membrane used in the next step. The mixture was heated to 50° C. and kept stirring for 18 h to allow a complete hydrolysis of TEOS. A small amount of sample was taken to analyze the hydrodynamic size and the chromatogram of newly formed particles by DLS and HPLC respectively.

The solution was concentrated by Vivaflow cassette (MWCO=5 kDa) to 200 ml. Then the pH of the solution was adjusted to 2 to break the ionic interaction between the unreacted DOTAGA and APTES-DOTAGA and the amines on the surface of newly formed nanoparticles. Solution was purified at this pH by Vivaflow for 50 purification rates with water as washing solvent (200 ml-1 L-200 ml-1 L-100 ml). After the purification, the solution was neutralized to pH 7.4 by adding drops of NaOH 1 M solution and filtered through 0.2 μm membrane to remove the dust and other large particles before being freeze-dried for long term storage. A small sample of purified solution was diluted 10 times in

TABLE 10

Characteristics and properties of UCHSNP-3, UCHSNP-4, UCHSNP-5 and UCHSNP-6

| Properties | Method(s) | UCHSNP-3 | UCHSNP-4 | UCHSNP-5 | UCHSNP-6 |
|---|---|---|---|---|---|
| Starting ratio A-D:A:T* | — | 14 A-D:6 A:0 T | 9.3 A-D:4 A:0.7 T | 7 A-D:3 A:10 T | 5.6 A-D:2.4 A:12 T |
| Total [silane] (mM) | | 20 | 20 | 20 | 20 |
| Solvent | | DMSO/H$_2$O | DMSO/H$_2$O | DMSO/H$_2$O | DMSO/H$_2$O |
| $D_H$ after synthesized (nm) | DLS | too weak signal | 5.2 ± 1.2 | 7.5 ± 2.1 | 13.6 ± 3.9 |
| $D_H$ redispersed pH 7 (nm) | DLS | 2.8 ± 0.5 | 4.3 ± 0.9 | 7.6 ± 1.9 | 14.4 ± 7.1 |
| Purity (%) | HPLC (295 nm) | 94.0 | 97.1 | 90.1 | 88.6 |
| DOTAGA content (μmol/mg) | Eu$^{3+}$ titration | 1.1 | 0.8 | 0.7 | 0.7 |
| $r_1$ (mM$^{-1}$·s$^{-1}$) (37° C., 60 MHz) | Relaxometry | — | 16.92 | 19.21 | 19.79 |
| $r_2/r_1$ (37° C., 60 MHz) | Relaxometry | — | 1.53 | 1.80 | 2.04 |
| Si:N:C (molar ratio) | Elemental analysis | — | 1.0:1.0:3.8 | 1.4:1.0:3.8 | 1.8:1.0:3.9 |
| A-D:A:T (molar ratio) | Elemental analysis | — | 1.0:3.4:3.6 | 1.0:3.7:7.1 | 1.0:2.4:10.0 |
| Yield (%) (in DOTAGA) | — | 1.15 | 7.94 | 12.20 | 15.41 |

*A-D: APTES-DOTAGA, A: APTES, T: TEOS, water right before being analyzed by DLS or in aqueous solution of TFA 0.1% before being analyzed by HPLC using UV absorption at 295 nm.

FIG. 21-A shows the DLS diagrams at different step during the synthesis: mixture of APTES and DOTAGA anhydride in DEG (dotted line, squares), the same mixture after adding TEOS (dotted line, up triangles), the mixture after diluted in water and heated overnight (dotted line, down triangles), the same mixture after filtered through 0.2 µm membrane (solid line, circles). FIG. 21-B shows the DLS diagram of the particle after purified by Vivaflow. The samples in DEG were first diluted 10 times in water and filtered to obtain homogeneous solutions instead of initial suspensions. As summarized in Table 11, $D_H$ of UCHSNP-7 changed during the synthesis process. Before TEOS was added, no particle was created indicating by small values of $D_H$ of 2 first samples (0.9 nm and 1.1 nm). After TEOS was introduced and hydrolyzed, it started to create ultrasmall cores on which the other organosilanes i.e. APTES and APTES-DOTAGA can now more stably graft. The final particle has $D_H$ around 4 nm.

TABLE 11

Summary of DLS results of UCHSNP-7 in different step during the synthesis

| Samples | $D_H$ (nm) |
|---|---|
| DOTAGA + APTES in DEG | 0.9 ± 0.4 |
| DOTAGA + APTES + TEOS in DEG | 1.1 ± 0.4 |
| DOTAGA + APTES + TEOS in H$_2$O | 4.7 ± 1.7 & 0.8 ± 0.2 |
| DOTAGA + APTES + TEOS in H$_2$O filtered | 4.1 ± 1.9 & 0.8 ± 0.2 |
| Final particle after purification | 4.1 ± 1.0 |

After the purification, the particles have almost the same hand slightly lower peak width which can be simply explained by the removal of physically absorbed silanes. The purity reached 98%. And the yield of the reaction and purification can be roughly estimated from the ratio between the peak areas of particles after purified and total peak areas of particles and reactants before purified which gave around 40%. For more quantitative insights, the data was summarized in Table 12.

TABLE 12

Summary of HPLC results of UCHSNP-7 before and after purified

| Samples | Purity (%) | $t_R$ (min) | Peak area (arb. unit) | FWHM (min) | Yield (%) |
|---|---|---|---|---|---|
| UCHSNP-7 before purified | 68.6 | 12.63 | 22797 | 1.1333 | |
| UCHSNP-7 after purified | 98.3 | 12.76 | 13617 (59.7%) | 0.8583 | 41.0 |

The DOTAGA content of UCHSNP-7 was determined by Eu titration as shown in FIG. 22. The result (~0.8 µmol/mg) was in accordance with the one found in particles with similar $D_H$ in previous examples. Combining this result with the total weight of produced particle (5.388 g), we can find out the yield of the process which is around 24.7% compared to the introduced quantity of DOTAGA. The nanoparticles UCHSNP-7 were also characterized by NMR, zeta potentiometry, relaxometry and elemental analysis. Table 13 summarizes the properties and characteristics of UCHSNP-7 and table 14 shows the zeta potential of UCHSNP-7 at different pHs. The full curve of the zeta potential at different pHs of UCHSNP-7 is presented in FIG. 24A.

TABLE 13

Characteristics and properties of UCHSNP-7

| Properties | Method(s) | UCHSNP-7 |
|---|---|---|
| Starting ratio A-D:A:T* | — | 7 A-D:8 A:20 T |
| Total [silane] (mM) | | 60 |
| Solvent | | DEG/H$_2$O |
| $D_H$ after synthesized (nm) | DLS | 4.1 ± 1.0 |
| $D_H$ redispersed pH 7 (nm) | DLS | 5.2 ± 2.0 |
| $D_H$ (nm) | NMR DOSY | 7.0 ± 2.5 (empty) |
| Zeta potential (mV) | Zeta potentiometry | Full curve −32.6 (pH 7.27) |
| Purity (%) | HPLC (295 nm) | 98.3 |
| DOTAGA content (µmol/mg) | Eu$^{3+}$ titration | 0.8 |
| $r_1$ (mM$^{-1}$ · s$^{-1}$) (37° C., 60 MHz) | Relaxometry | — |
| $r_2/r_1$ (37° C., 60 MHz) | Relaxometry | — |
| A/A-D | $^1$H NMR | 1.26 (empty) |
| Si:N:C (molar ratio) | Elemental analysis | 1.1:1.0:4.4 |
| A-D:A:T (molar ratio) | Elemental analysis | 1.0:1.0:4.7 |
| Yield (%) (in DOTAGA) | — | 24.7 |

*A-D: APTES-DOTAGA, A: APTES, T: TEOS

TABLE 14

Zeta potential of empty UCHSNP-7 at different pHs

| pH | Zeta potential (mV) |
|---|---|
| 2.21 | 37.2 |
| 3.23 | 17.3 |
| 4.21 | 0.558 |
| 5.25 | −19.9 |
| 6.22 | −26 |
| 6.75 | −27.1 |
| 7.27 | −32.6 |
| 7.78 | −31.5 |
| 8.26 | −32.4 |

Complexation of UCHSNP-7 with Different Metals (Gd, Ho, Tb and Bi)

283 mg of lyophilized powder of UCHSNP-7 containing 227 µmol DOTAGA, was redispersed in water to have a concentration around 200 mM of DOTAGA. pH of the solution was adjusted to 5.5 by adding NaOH solution with appropriate concentrations. 98.5 µl of GdCl$_3$ solution at 2.188 M (molar ratio DOTAGA:Gd=1:0.95) was added slowly in 3 times while the solution was heated and stirred on a heat plate at 70° C. to speed up the complexation. Between each time, pH was carefully increased to 5-5.5 by adding slowly NaOH solutions before adding the next one. After 3 additions, water was added to obtain a concentration of 100 mM of DOTAGA and a pH around 5-5.5. This solution was stirred in an oil bath at 80° C. for 18 h. After the incubation, pH maintained at around 5.5. This solution was purified with water as solvent by tangential filtration (MWCO=3 kDa) with 16 purification rates to get rid of any free $Gd^{3+}$. Finally, the solution was neutralized to pH 7 by adding few drops of NaOH solutions and filtered through 0.2 µm membrane to remove the dust and other large particles before being freeze-dried for long term storage. A small sample of purified solution was diluted 10 times in water right before being analyzed by DLS.

Similar protocols were applied using 431 µl of $HoCl_3$ or $TbCl_3$ solutions at 500 mM instead.

For Bi particles, due to a very limited solubility of bismuth hydroxide, 817 µl of $BiCl_3$ solutions at 250 mM in HCl 6 M was used. The nanoparticles solution had to be heated at 70° C. before any addition was carried out to increase the solubility of $Bi^{3+}$ and the speed of the complexation. Failures to maintain this condition might induce the formation of bismuth hydroxide precipitates. NaOH solution at 10 M was needed to neutralize the solution to pH 5-5.5 and solution was heated in an oil bath at 80° C. for 1 h between each step of addition. The rest of the protocol was similar.

Figure 23:
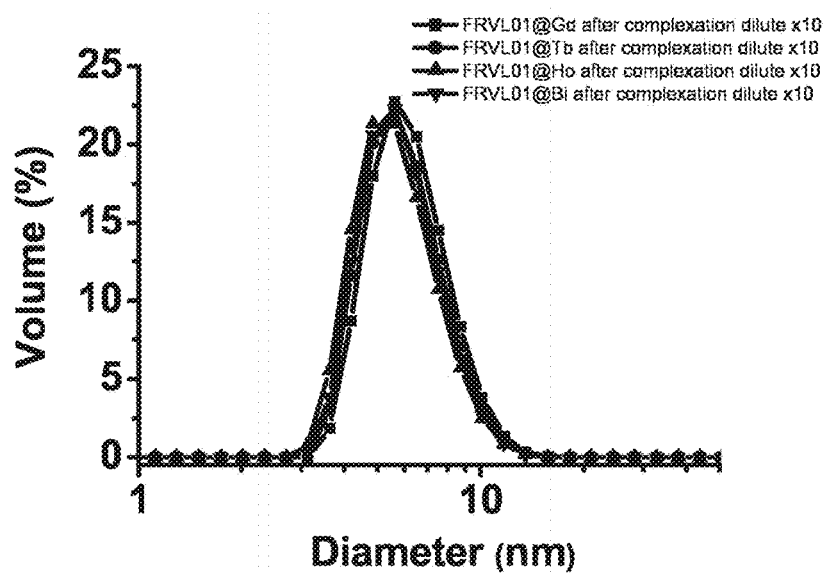
FIG. 23 shows the DLS diagrams of UCHSNP-7@M (M: Gd (squares), Tb (circles), Ho (up triangles) and Bi (down triangles)) according to example 4.

FIG. 23 shows the DLS diagram of UCHSNP-7@M (M: Gd, Tb, Ho or Bi). The results were quantitatively presented in Table 15. All of 4 particles have a hydrodynamic diameter around 6 nm. The results were in accordance with example 1 where UCHSNP@Gd-1 also had $D_H$ about 6 nm.

TABLE 15

Summary of the DLS results of UCHSNP-7@M

| Samples | $D_H$ (nm) |
|---|---|
| UCHSNP-7@Gd | 6.3 ± 1.7 |
| UCHSNP-7@Tb | 6.1 ± 1.7 |
| UCHSNP-7@Ho | 5.8 ± 1.6 |
| UCHSNP-7@Bi | 6.0 ± 1.6 |

The purified solution of Bi particle (UCHSNP-7@Bi) was diluted 15 times in aqueous solution of TFA 0.1% before being analyzed by HPLC (method 1).

The peak of nanoparticles was found at $t_R$=15.7 min which is very similar to UCHSNP@Gd-1. Gd-1. The shape of the peak also shows a homogenous distribution after the complexation. The purity of the particles was very high (97.4%). This chromatogram was normalized to the same height as UCHSNP-7 to compare the retention time (Wand peak width (FWHM). The 2 values of complexed particles were both higher than the ones of the empty particles. The results were summarized in Table 16.

TABLE 16

Summary of HPLC results of UCHSNP-7 before and after complexed with Bi

| Samples | Purity (%) | $t_R$ (min) | FWHM (min) |
|---|---|---|---|
| UCHSNP-7 after purified | 98.3 | 12.76 | 0.8583 |
| UCHSNP-7@Bi after purified | 97.4 | 15.74 | 2.7417 |

Figure 24:
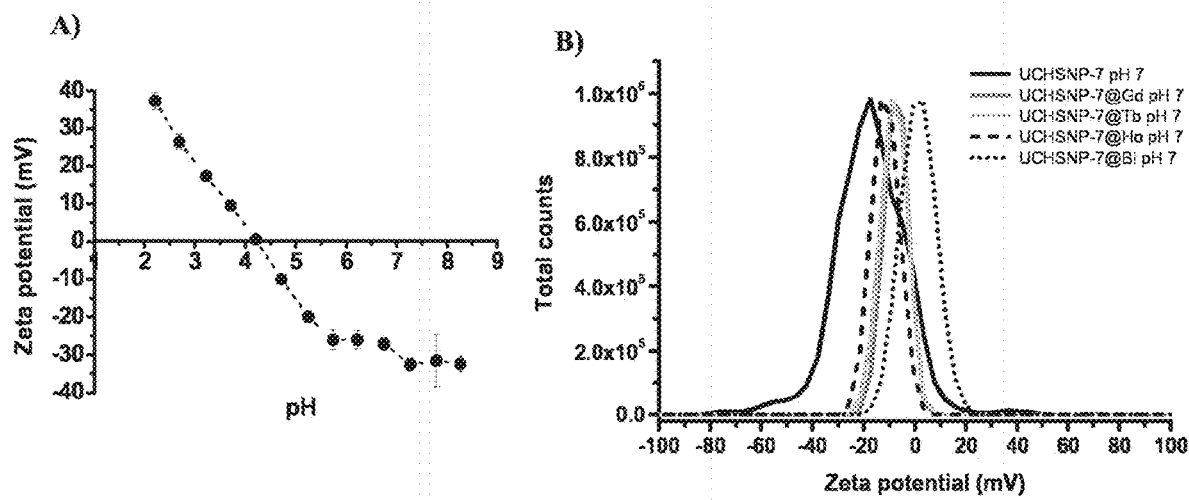
FIG. 24A shows the full curve of zeta potential at different pHs of UCHSNP-7 according to example 4.
FIG. 24B shows the zeta potential of UCHSNP-7@Gd, UCHSNP-7@Tb, UCHSNP-7@Ho and UCHSNP-7@Bi at pH 6.6 according to example 4.
Figure 25:
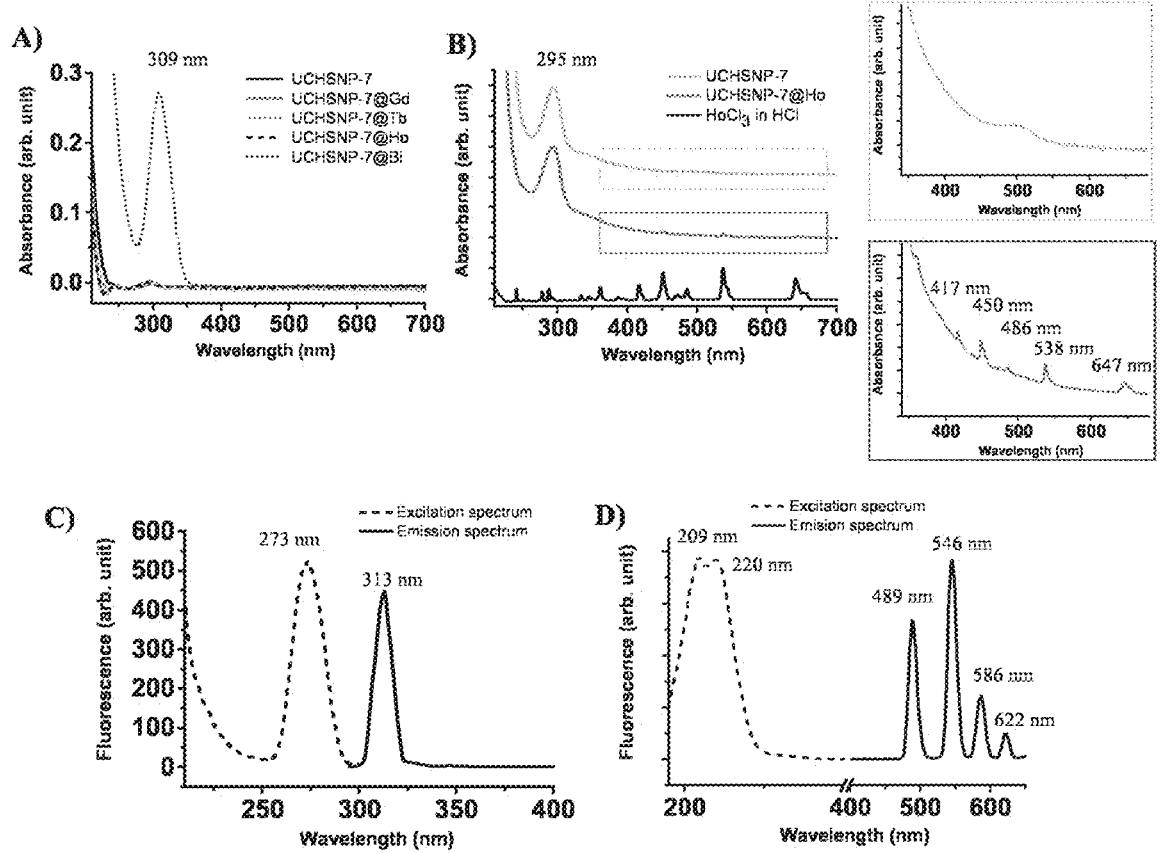
FIG. 25A shows the UV-visible absorption spetra of UCHSNP-7, UCHSNP-7@Gd, UCHSNP-7@Tb, UCHSNP-7@Ho and UCHSNP-7@Bi according to example 4.
FIG. 25B shows the UV-visible absorption spetra of UCHSNP-7, UCHSNP-7@Ho and $HoCl_3$ at 50 mM in HCl 0.1 mM, according to example 4.
FIG. 25C shows the UV-visible excitation and emission spectra of UCHSNP-7@Gd according to example 4.
FIG. 25D shows the UV-visible excitation and emission spectra of UCHSNP-7@Tb according to example 4.
Figure 26:
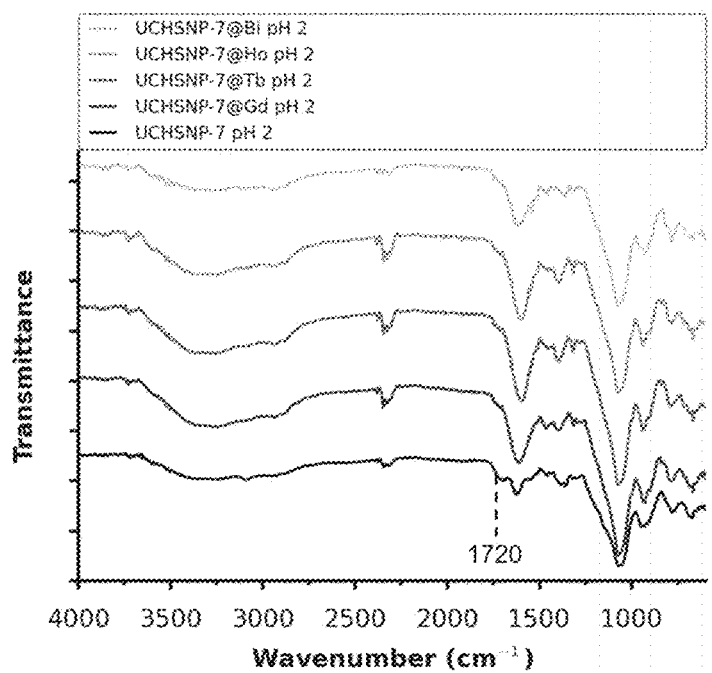
FIG. 26 shows the IR spetra of UCHSNP-7, UCHSNP-7@Gd, UCHSNP-7@Tb, UCHSNP-7@Ho and UCHSNP-7@Bi according to example 4.

The nanoparticles UCHSNP-7@Gd, UCHSNP-7@Tb, UCHSNP-7@Ho and UCHSNP-7@Bi were also characterized by zeta potentiometry, relaxometry, ICP-EOS, UV-visible spectroscopy and IR spectroscopy. Table 17 summarizes the properties and characteristics of UCHSNP-7. The zeta potential of the nanoparticles at pH 6.6 is shown in FIG. 24B. The UV-visible spectra of the nanoparticles are shown in FIG. 25. Sample of UCHSNP-7@Bi showed an intense peak at 309 nm which is typical for $DOTA(Bi^{3+})$ complex. UV-vis spectrum of UCHSNP-7@Ho shows several absorption peaks of $Ho^{3+}$. The IR spectra are shown in FIG. 26. They confirm the presence of metals.

TABLE 17

Properties of metals complexed UCHSNP-7

| Properties | Method(s) | UCHSNP-7@Gd | UCHSNP-7@Tb | UCHSNP-7@Ho | UCHSNP-7@Bi |
|---|---|---|---|---|---|
| Starting ratio A-D:A:T (:M)* | — | 7 A-D:8 A:20 T:6.6 Gd | 7 A-D:8 A:20 T:6.6 Tb | 7 A-D:8 A:20 T:6.6 Ho | 7 A-D:8 A:20 T:6.3 Bi |
| $D_H$ (nm) | DLS | 6.3 ± 1.7 | 6.1 ± 1.7 | 5.8 ± 1.6 | 6.0 ± 1.6 |
| Zeta potential (mV) | Zeta potentiometry | −6.9 (pH 6.65) | −7.9 (pH 6.64) | −12.0 (pH 6.65) | 2.3 (pH 6.67) |
| | | −21.8 (pH 7.36) | −19.3 (pH 7.39) | −19.8 (pH 7.42) | −3.4 (pH 7.35) |
| Purity (%) | HPLC (295 nm) | 96.6 | 98.3 | 97.3 | 97.4 |
| $r_1$ ($mM^{-1} \cdot s^{-1}$) (37° C., 60 MHz) | Relaxometry | 23.23 | — | — | — |
| $r_2/r_1$ (37° C., 60 MHz) | Relaxometry | 1.65 | — | — | — |
| M content (µmol/mg) | ICP-OES | 0.654 | 0.558 | 0.625 | 0.442 |
| A-D:A:T:M | Assumption | 1.0 A-D:1.0 A:4.7 T:0.7 Gd | 1.0 A-D:1.0 A:4.7 T:0.6 Tb | 1.0 A-D:1.0 A:4.7 T:0.7 Ho | 1.0 A-D:1.0 A:4.7 T:0.5 Bi |
| Yield (%) (in metal) | — | 69.2 | 62.7 | 68.2 | 51.2 |

*A-D: APTES-DOTAGA, A: APTES, T: TEOS, M: metal (Gd, Tb, Ho or Bi)

Example 5: In Vivo Magnetic Resonance Imaging (MRI) Experiment

Three BALB/c mice were inoculated subcutaneously with colon carcinoma (CT26) cells on both flanks.

UCHSNP@Gd-2 lyophilized powder was dispersed in physiological serum at 100 mM (in Gd). This concentrated solution was diluted to 20 mM in serum before being injected intravenously to the mice at the dose of 200 μmol (in Gd) per kg.

Images were acquired before (pre-contrast) and after injection (post-contrast) using a 7 T MRI system 300WB micro imaging spectrometer, with a 1H 40 mm coil, Paravision 5.11 software (Bruker, Germany). The respiratory rate was continuously monitored by adjusting isoflurane concentration (1.5%) Dynamic contrast enhanced (DCE) sequence was recorded using Intragate Flash multislices for motion free artifacts with TR=100 ms, TE=4 ms, flip angle=80°. The repetition number was set to 15 and a number of time frames to reconstruct was 1. A field-of-view (FOV) of 3 cm×3 cm and a matrix of 256×256, 4 slices with a thickness of 1 mm were chosen, giving a spatial resolution of 117 μm×117 μm in plane. The total scan time was in the order of 3 min 14 sec. Finally, an elongated version of the Intragate Flash multislices sequence was used for the dynamic follow-up to obtain the same temporal resolution in a scan time of 40 min. 2-3 min scans were performed 3-6 hours post-contrast as follow up.

Several regions of interest (ROI) in tumors and liver were monitored and the MRI intensities of ROIs were plotted pre- and post-injection of the particle. Tissue enhancement level of the signal in each tissue area was calculated as (St−S0)/S0, where St was the signal intensity measured at each time point after injection, and S0 was the signal intensity before injection.

Figure 27:
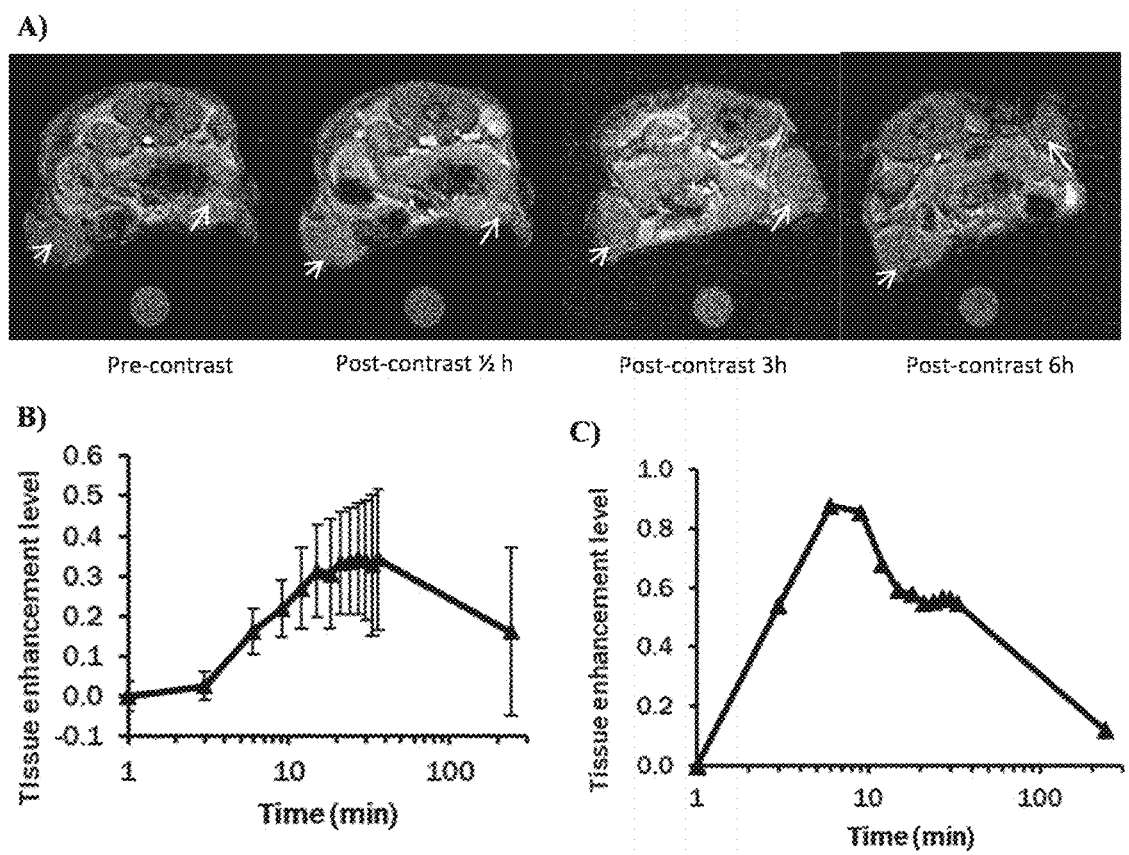
FIG. 27A shows the MRI cross-sections of the tumor tissues (white arrows) pre-(left) and post-injection (right, up to 6 h) of UCHSNP@Gd-2 according to example 5.
FIG. 27B shows the dynamic MRI signal enhancement in tumor tissues after injection of UCHSNP@Gd-2 according to example 5.
FIG. 27C shows the dynamic MRI signal enhancement in the liver after injection of UCHSNP@Gd-2 according to example 5.

FIG. 27A shows MRI cross-sections where the tumor regions are highlighted as expected. Comparison of the pre- and post-contrast images clearly reveals the higher brightness at the tumor regions caused by the particle. Contrast enhancement was expressed as percentage of enhancement compared to the pre-contrast image. In the tumor tissue, UCHSNP@Gd-2 showed an intake phase with a maximal enhancement 30 minutes post injection (35% of signal increase) and a prolonged clearance phase, with a half-time of 3 hours, demonstrating the EPR (Enhanced Permeability and Retention) effect (See FIG. 27B). In the liver, peak of enhancement (90% increase of signal) was observed at 6 minutes post-injection of the particle followed by a clearance phase (See FIG. 27C). After 40 min post-injection, the signal was at half of maximal intensity, indicating a hepatic half-time around 30 minutes. After bloodstream circulation with a complementary transitory visualization through the vascular network in the liver, particles were excreted from the kidney cortex to the bladder as previously shown with ultrasmall nanoparticles.

This imaging study evidences that UCHSNP@Gd-2 displays contrast enhancement in both the tumors and hepatic tissues over the full observation period, without the typical liver accumulation observed for macromolecular agents. Thus, they improve the imaging properties without undesired liver uptake. Meanwhile, the relatively long retention time in the tumors opens the perspective for vectorization towards tumor tissues.

The invention claimed is:

1. A method for synthesizing silica nanoparticles, said method comprising the mixing of at least one silane which is negatively charged at physiological pH with at least one silane which is neutral at physiological pH, and/or
at least one silane which is positively charged at physiological pH,
wherein:
the molar ratio A of neutral silane(s) to negatively charged silane(s) is defined as follows: 0≤A≤6;
the molar ratio B of positively charged silane(s) to negatively charged silane(s) is defined as follows: 0≤B≤5;
the molar ratio C of neutral and positively charged silanes to negatively charged silane(s) is defined as follows: 0<C≤8, wherein said nanoparticles, dispersed in water, have a mean hydrodynamic diameter between 0.5 and 15 nm, and wherein all the silanes represent at least 80% by weight of the total weight of the reagents.

2. The method according to claim 1, wherein all the silanes are chosen among alkoxysilanes, hydroxysilanes, and mixture thereof.

3. The method according to claim 1, wherein the mixing step is performed in a protic solvent.

4. The method according to claim 1, wherein said method is a one-pot synthesis without any isolation or purification step of the intermediate product(s).

5. The method according to claim 1, wherein the silica nanoparticles do not comprise a crystalline core.

6. The method according to claim 1, wherein said negatively charged silane(s) includes silane(s) comprising at least one, two, or more negatively charged carboxylic acid functions.

7. The method according to claim 1, wherein said negatively charged silane(s) includes silane(s) comprising at least one chelating agent.

8. The method according to claim 7, wherein said chelating agent is chosen from polyamino polycarboxylic acids including without limitation:

DOTA (1,4,7,10-tetraazacyclododecane-N,N',N'',N'''-tetraacetic acid), DOTAGA (2-(4,7,10-tris(carboxymethyl)-1,4,7,10-tetraazacyclododecan-1-yl)pentanedioic acid), DO3A-pyridine of formula (III) below:

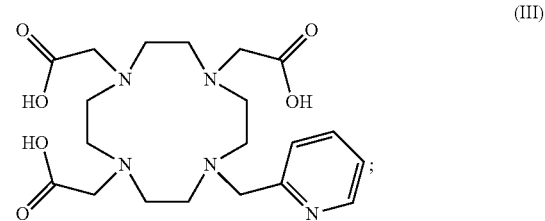 [SMILES: O=C(O)CN1CCN(CC(=O)O)CCN(Cc2ccccn2)CCN(CC(=O)O)CC1]

DTPA (diethylenetriaminepentaacetic acid), CHX-DTPA (trans-cyclohexyl-diethylenetriaminepentaacetic acid), oxo-Do3A (1-oxa-4,7,10-triazacyclododecane-4,7,10-triacetic acid), SCN-Bz-DTPA (p-isothiocyanatobenzyl-DTPA), 1 B3M (1-(p-isothiocyanatobenzyl)-3-methyl-DTPA), MX-DTPA (1-(2)-methyl-4-isocyanatobenzyl-DTPA);
EDTA (2,2',2'',2'''-(ethane-1,2-diyldinitrilo)tetraacetic acid);
EGTA (ethylene glycol-bis(2-aminoethylether)-N,N,N',N'-tetraacetic acid), BAPTA (1,2-bis(o-aminophenoxy)ethane-N,N,N',N'-tetraacetic acid);
NOTA (1,4,7-triazacyclononane-1,4,7-triacetic acid);
PCTA (3,6,9,15-tetraazabicyclo[9.3.1.]pentadeca-1(15),11,13-triene-3,6,9-triacetic acid);

TMPAC of formula (N) below:

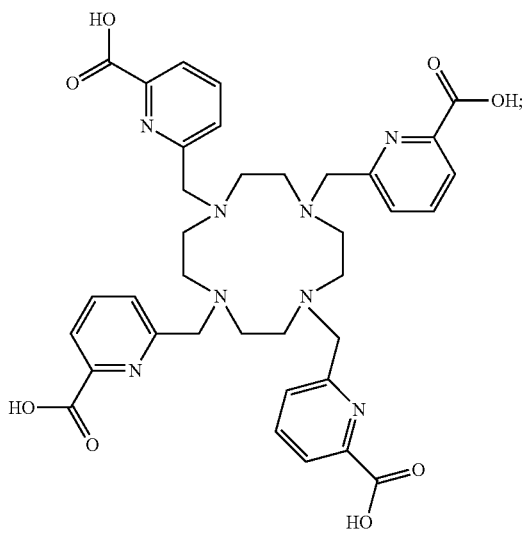

(IV)

and mixtures thereof.

9. The method according to claim 7, wherein said chelating agent(s) is(are) free of metallic ions.

10. The method according to claim 7, wherein said chelating agent(s) is(are) chelating a metallic ion including alkali metal ions and their radioactive isotopes, transition metal ions and their radioactive isotopes, post-transition metal ions and their radioactive isotopes, rare earth metal ions and their radioactive isotopes, and mixtures thereof.

11. The method according to claim 1, wherein said positively charged silane(s) includes at least a silane with one positively charged amino function.

12. The method according to claim 1, wherein the mixing step further includes at least one silane comprising at least one fluorophore, the molar ratio D of silane(s) comprising a fluorophore to neutral silane(s) being defined as follows: $0.001 \leq D \leq 0.2$.

13. The method according to claim 1, wherein the mixing step further includes at least one silane comprising at least one drug moiety, the molar ratio E of silane(s) comprising a drug to neutral silane(s) is defined as follows: $0.1 \leq E \leq 5$.

14. Method according to claim 13, wherein the nanoparticles comprise between 0.5 and 50% by weight of drug moiety as compared to the total weight of the nanoparticle.

15. The method of claim 1, wherein the molar ratio A of neutral silane(s) to negatively charged silane(s) is defined as follows: $0.5 \leq A \leq 2$.

16. The method of claim 1, wherein the molar ratio B of positively charged silane(s) to negatively charged silane(s) is defined as follows: $0.25 \leq B \leq 3$.

17. The method of claim 1, wherein the molar ratio C of neutral and positively charged silanes to negatively charged silane(s) is defined as follows: $1 < C \leq 4$.

18. The method of claim 1, wherein said nanoparticles, dispersed in water, have a mean hydrodynamic diameter between 0.5 and 10 nm.

19. The method of claim 13, wherein the nanoparticles comprise between 2 and 10% by weight of drug moiety as compared to the total weight of the nanoparticle.

* * * * *